US010234364B2

(12) United States Patent
Nagai et al.

(10) Patent No.: US 10,234,364 B2
(45) Date of Patent: Mar. 19, 2019

(54) SAMPLE PROCESSING APPARATUS AND RACK

(71) Applicant: SYSMEX CORPORATION, Kobe-shi, Hyogo (JP)

(72) Inventors: Takaaki Nagai, Kobe (JP); Daigo Fukuma, Kobe (JP); Mitsuo Yamasaki, Kobe (JP); Noriyuki Nakanishi, Kobe (JP); Syunsuke Yao, Kobe (JP); Tomonori Okazaki, Kobe (JP); Takahiro Saino, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 15/637,121

(22) Filed: Jun. 29, 2017

(65) Prior Publication Data

US 2017/0363521 A1   Dec. 21, 2017

Related U.S. Application Data

(63) Continuation of application No. 14/580,888, filed on Dec. 23, 2014, now Pat. No. 9,733,161.

(30) Foreign Application Priority Data

Dec. 27, 2013   (JP) .................................. 2013-272561

(51) Int. Cl.
 *G01N 1/28* (2006.01)
 *G01N 35/04* (2006.01)
 (Continued)

(52) U.S. Cl.
 CPC .................. *G01N 1/28* (2013.01); *B01L 9/06* (2013.01); *G01N 35/04* (2013.01);
 (Continued)

(58) Field of Classification Search
 CPC ........... G01N 35/0095; G01N 35/0099; G01N 35/02; G01N 35/04; G01N 2035/0401;
 (Continued)

(56) References Cited

U.S. PATENT DOCUMENTS 6,060,022 A * 5/2000 Pang .................. G01N 35/0095
 422/63
6,919,044 B1 * 7/2005 Shibata .............. G01N 35/0092
 422/63

(Continued)

FOREIGN PATENT DOCUMENTS

JP   H05-180732 A   7/1993
JP   2012-251883 A   12/2012

*Primary Examiner* — Brian R Gordon
(74) *Attorney, Agent, or Firm* — Metrolexis Law Group, PLLC

(57) ABSTRACT

First and second racks each has fixed positions to hold sample tubes. First and second drawers slide into and out of the case, and that support the first and second racks, respectively. A tube set unit is provided in an area close to the first rack in the case. A tube transfer unit removes sample tubes from the first and second racks in the case and a controller that controls a transfer operation of the tube transfer unit. The first rack is supported by the first drawer such that the first rack leaves a transit location in the case behind the first drawer in the direction of the first drawer movement into the case. The controller controls the tube transfer unit to remove at least one sample tube from the second rack and transfers the tube to the tube set unit via a path traversing the transit location.

19 Claims, 15 Drawing Sheets

(51) Int. Cl.
  *G01N 35/00* (2006.01)
  *B01L 9/06* (2006.01)
(52) U.S. Cl.
  CPC . *G01N 35/0099* (2013.01); *G01N 2035/0412* (2013.01); *G01N 2035/0498* (2013.01)
(58) Field of Classification Search
  CPC .... G01N 2035/0406; G01N 2035/0412; B01L 9/06; B01L 9/065
  See application file for complete search history.

(56) References Cited

U.S. PATENT DOCUMENTS

| | | | | |
|---|---|---|---|---|
| 2006/0148063 | A1* | 7/2006 | Fauzzi | G01N 1/31 435/286.4 |
| 2009/0142844 | A1* | 6/2009 | Le Comte | G01N 35/00594 436/8 |
| 2013/0330254 | A1 | 12/2013 | Jensen et al. | |

* cited by examiner

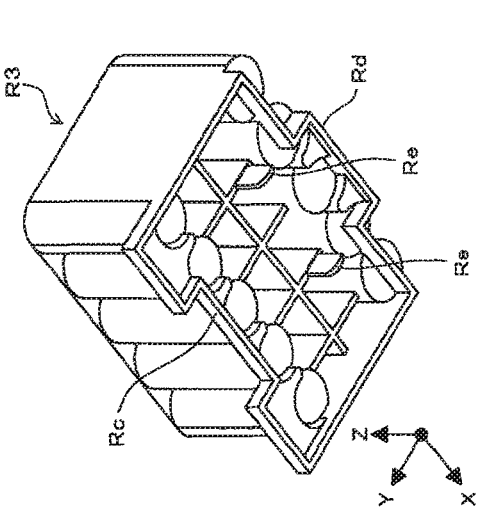
FIG.4A FOR REGULAR SAMPLE TUBE T1
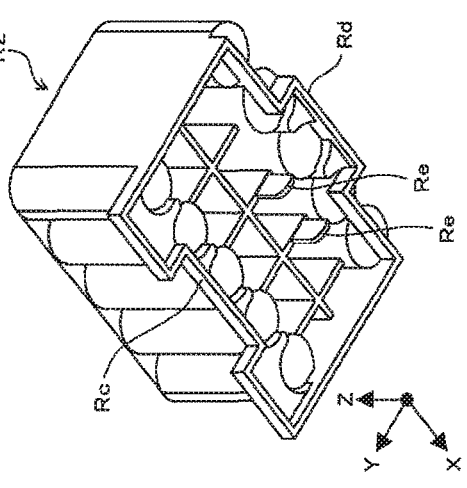
FIG.4B FOR REGULAR SAMPLE TUBE T2
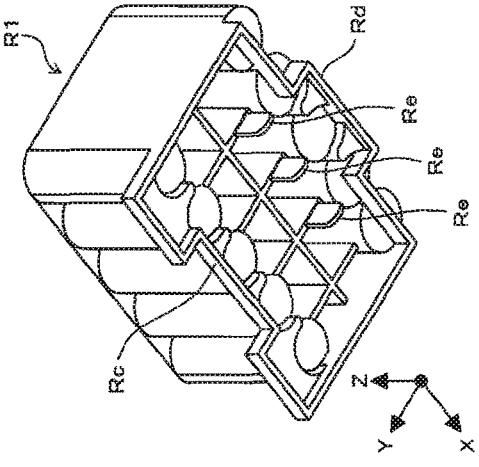
FIG.4C FOR REGULAR SAMPLE TUBE T3
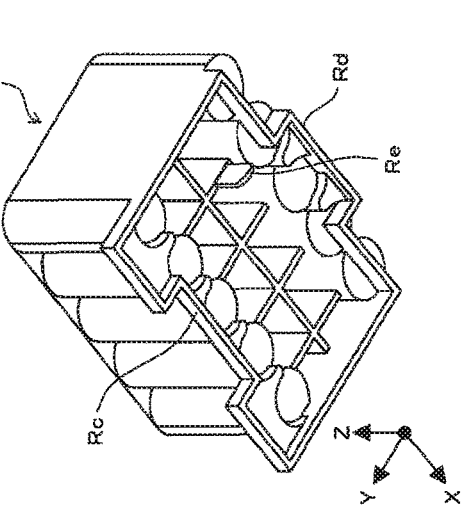
FIG.4D FOR PRIORITY SAMPLE TUBE T1
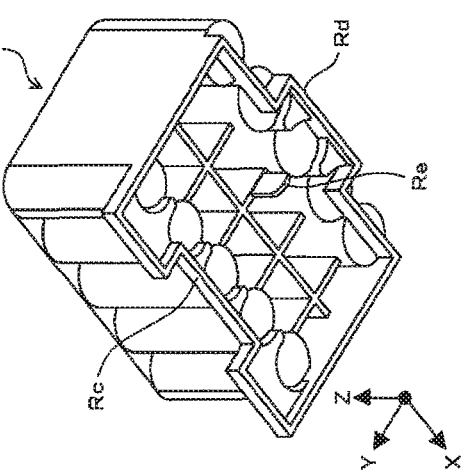
FIG.4E FOR PRIORITY SAMPLE TUBE T2
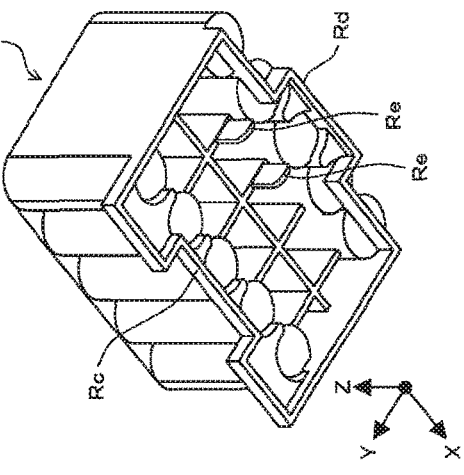
FIG.4F FOR PRIORITY SAMPLE TUBE T1

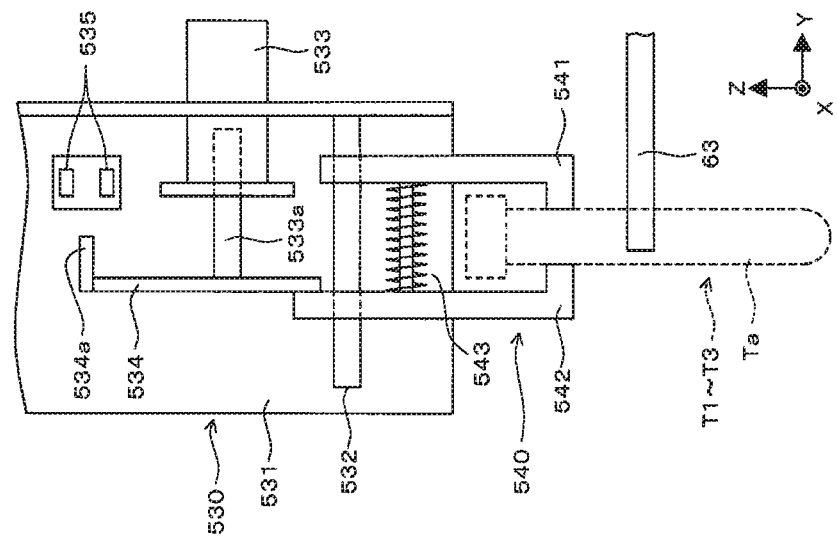
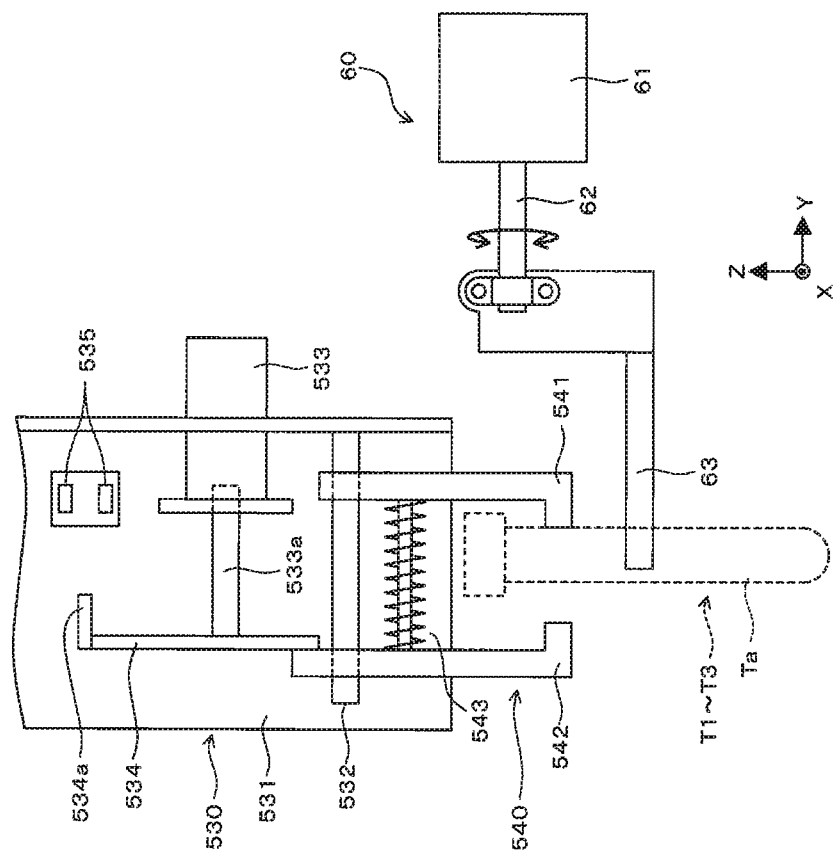

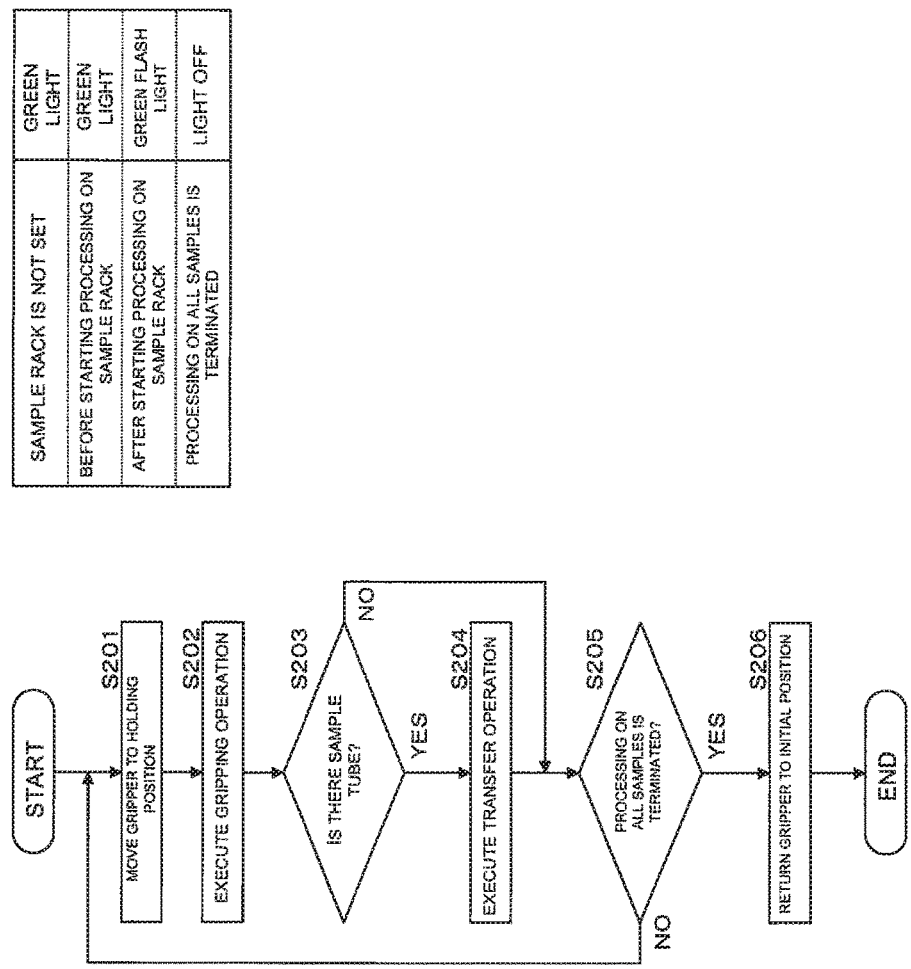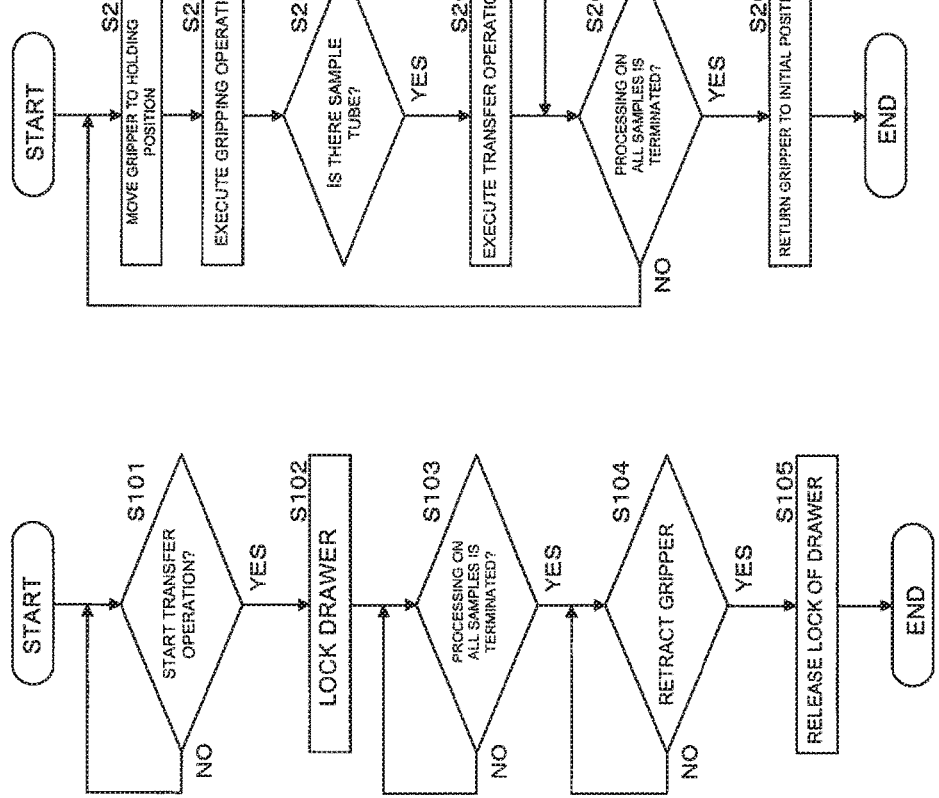

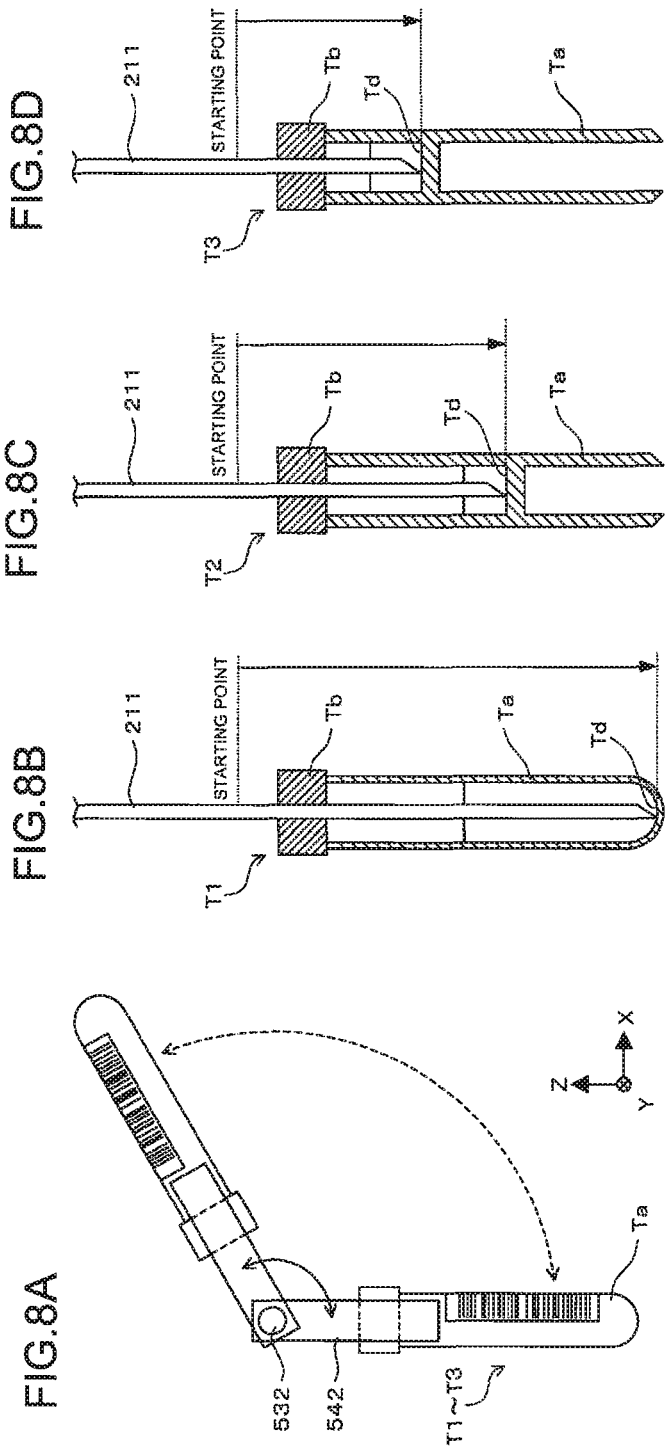

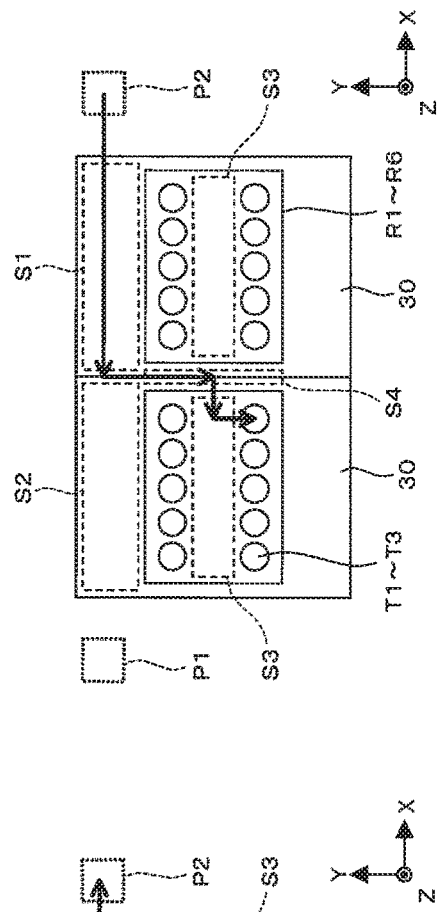
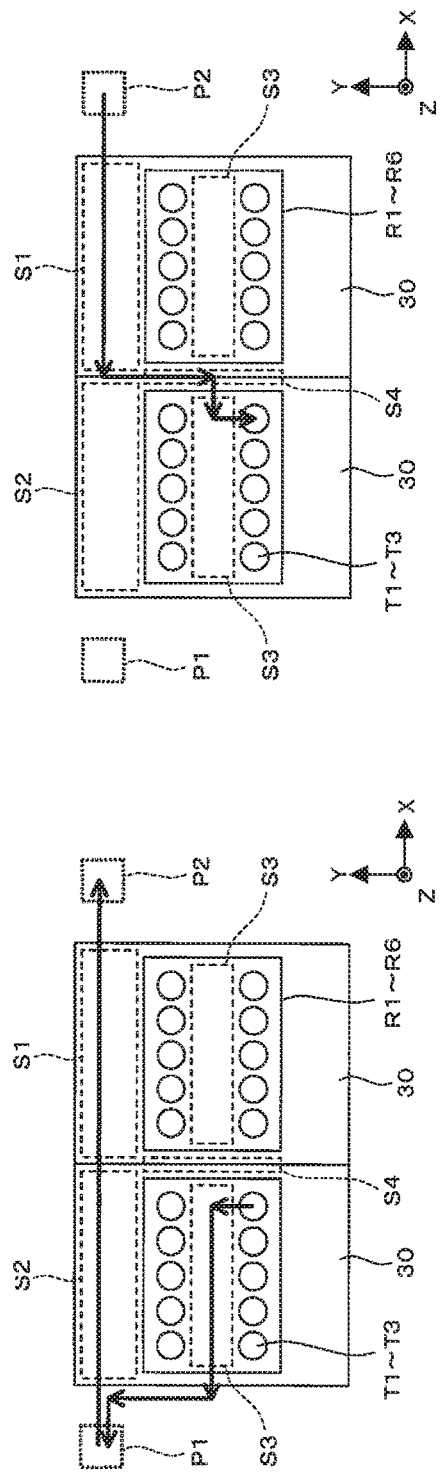
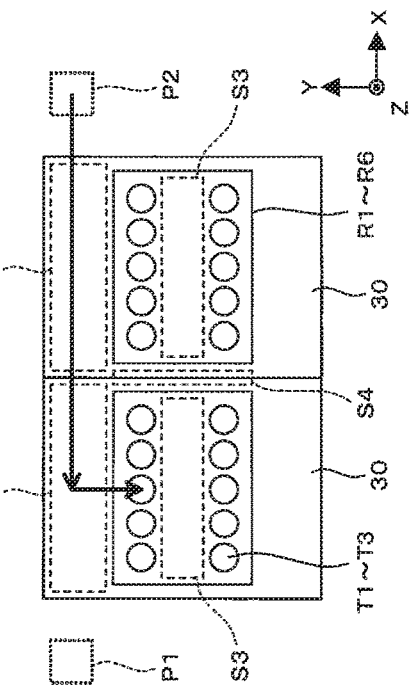
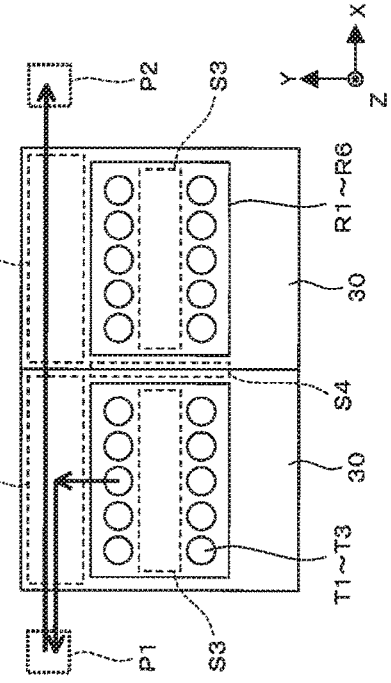

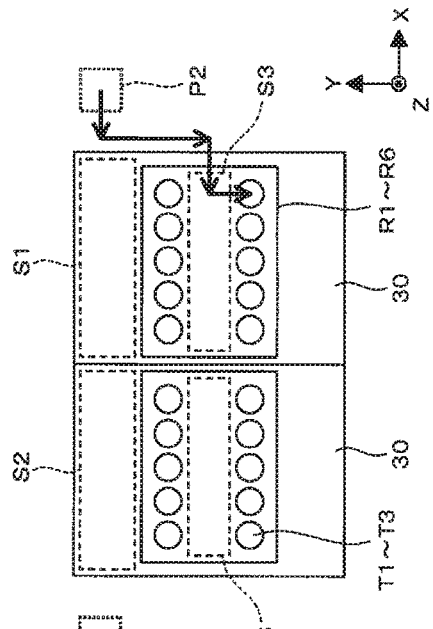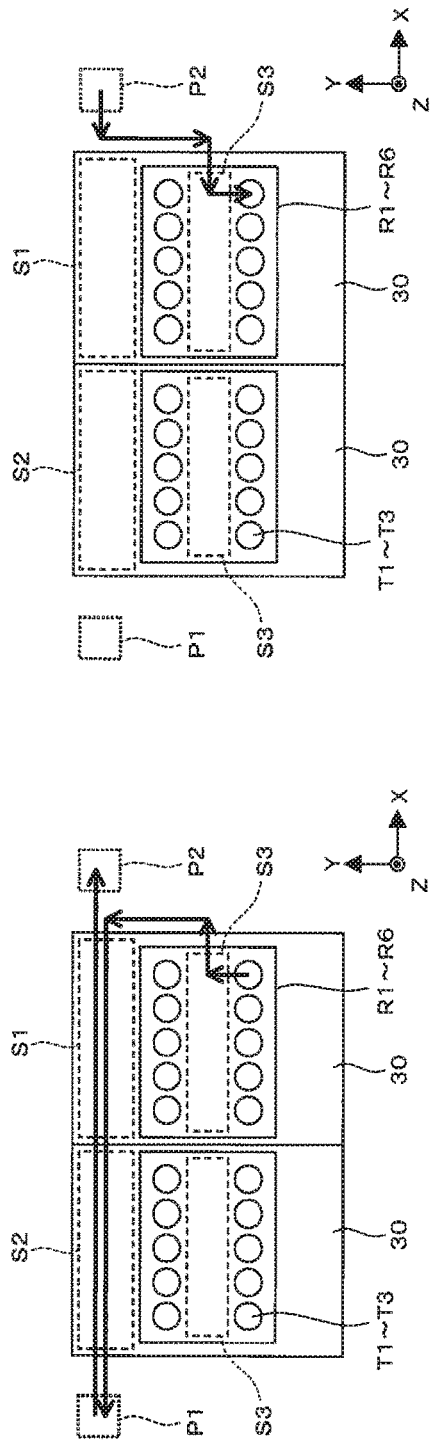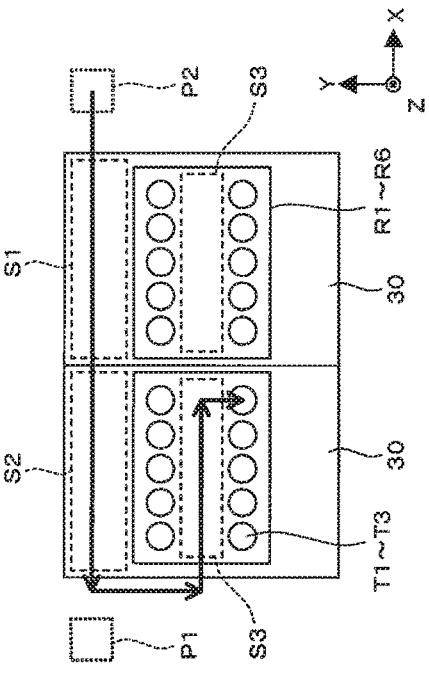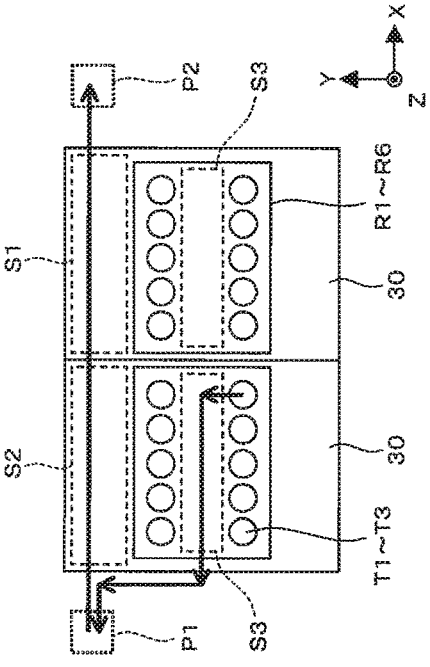

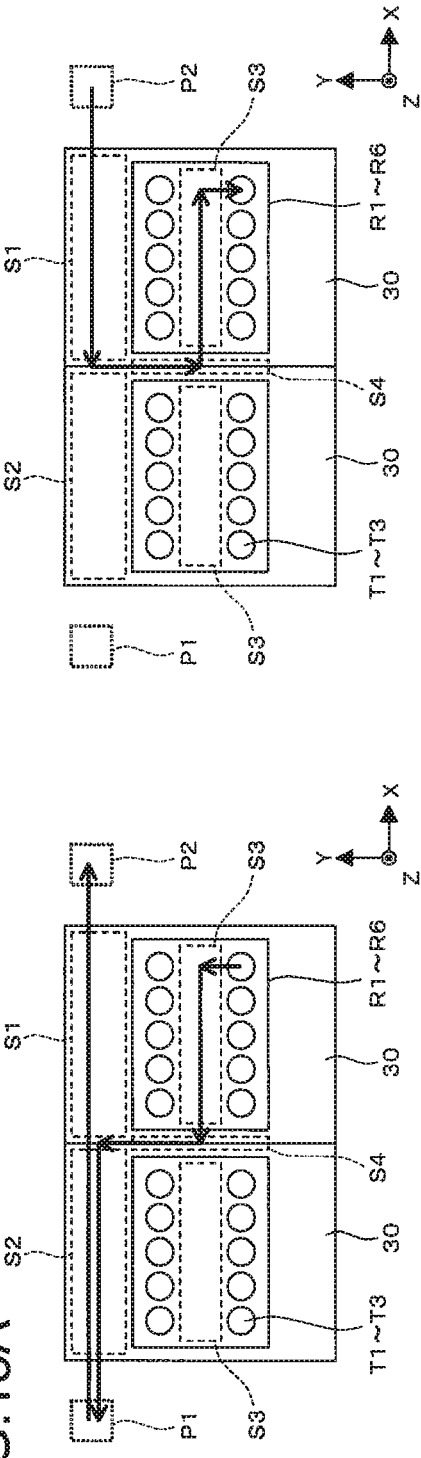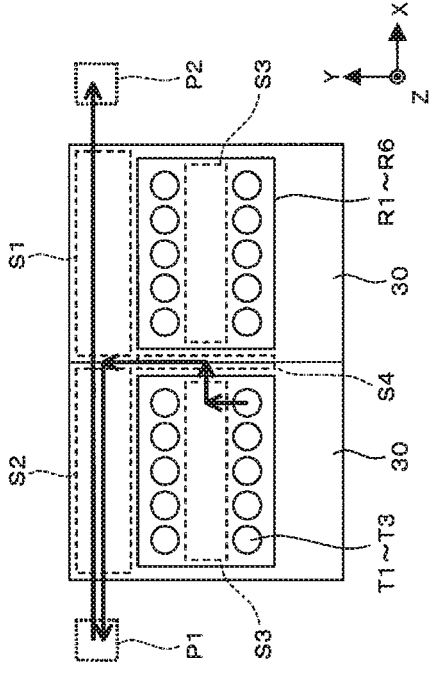

SAMPLE PROCESSING APPARATUS AND RACK

This application is a continuation of application Ser. No. 14/580,888, filed on Dec. 23, 2014, now U.S. Pat. No. 9,733,161 which is based upon and claims the benefit of priority from the prior Japanese Patent Application No. 2013-272561, filed on Dec. 27, 2013, the entire contents of all of which are incorporated herein by reference.

FIELD OF THE INVENTION

The invention relates to a sample processing apparatus configured to perform processing on a sample held in a sample tube and a rack, which is used for the sample processing apparatus.

BACKGROUND

There is known a sample analyzer in which a sample tube supply unit transfers one of multiple sample tubes held in a rack to a sample rack set unit and sets the sample tube in the sample rack set unit, a sample in the set sample tube is aspirated, and a measurement unit measures the aspirated sample (see Japanese Patent Application Publication No. 2007-139462).

In the sample analyzer, in order for an operator to accommodate sample tubes in a rack, the operator needs to accommodate the sample tubes after waiting for an analyzer unit to complete measurement. In addition, it also takes some time to accommodate the sample tubes. For these reasons, some of facilities which have to process a large number of samples are subject to deterioration of sample processing performance of the device.

SUMMARY OF THE INVENTION

The scope of the invention is defined by the appended claims, and not by any statements within this summary.

A first embodiment relates to a sample processing apparatus. The sample processing apparatus according to this embodiment includes a case, first and second racks each configured to hold sample tubes, first and second drawers being capable of sliding into and out of the case, and configured to support the first and second racks, respectively, a tube set unit provided in an area close to the first rack in an entire area inside the case, a tube transfer unit configured to take out the sample tubes from each of the first and second racks in the case, and a controller configured to control a transfer operation of the tube transfer unit. The first rack in a state drawn in the case is supported by the first drawer so that the first rack leaves a first space on a side in a direction to which the first drawer is drawn into the case. The controller controls the tube transfer unit so that at least one of the sample tubes is taken out from the second rack and is transferred to the tube set unit through a transfer path passing the first space.

A second aspect of the invention relates to a rack. The rack of this aspect may have a configuration in which tube holders are arranged in rows, and a space large enough to transfer at least a sample tube is provided between adjacent two of the rows.

BRIEF DESCRIPTION OF DRAWINGS

FIGS. 4A to 4F are perspective diagrams, each illustrating a case where the rack according to the embodiment is seen from below;

FIGS. 6A and 6B are schematic diagrams, each illustrating a case where a vertical movement unit, holder, and stirrer mechanism are seen in the X-axis negative direction;

FIG. 7A is a flowchart illustrating lock processing on a drawer;

FIG. 7B is a flowchart illustrating transfer processing on a sample tube;

FIG. 7C is a diagram illustrating lamp lighting processing;

FIG. 8A is a diagram illustrating stirring processing by a stirrer mechanism according to the embodiment;

FIGS. 8B to 8D are diagrams, each illustrating aspiration processing by an aspiration unit according to the embodiment;

FIG. 8E is a conceptual diagram illustrating a configuration of a setting table stored in a hard disk according to the embodiment;

FIGS. 12A to 12D are diagrams, each illustrating a path in which sample tubes held in a left rack according to the embodiment are transferred by the tube transfer unit;

FIGS. 14A to 14D are diagrams, each illustrating a path in which sample tubes held in a rack according to the modified embodiment are transferred by the tube transfer unit; and FIGS. 15A to 15D are diagrams, each illustrating a path in which sample tubes held in the rack according to the modified embodiment are transferred by the tube transfer unit.

DETAILED DESCRIPTION

One embodiment is a sample analyzer configured to examine and analyze blood. Hereinafter, a sample analyzer according to the embodiment is described by referring to drawings.

Figure 1:
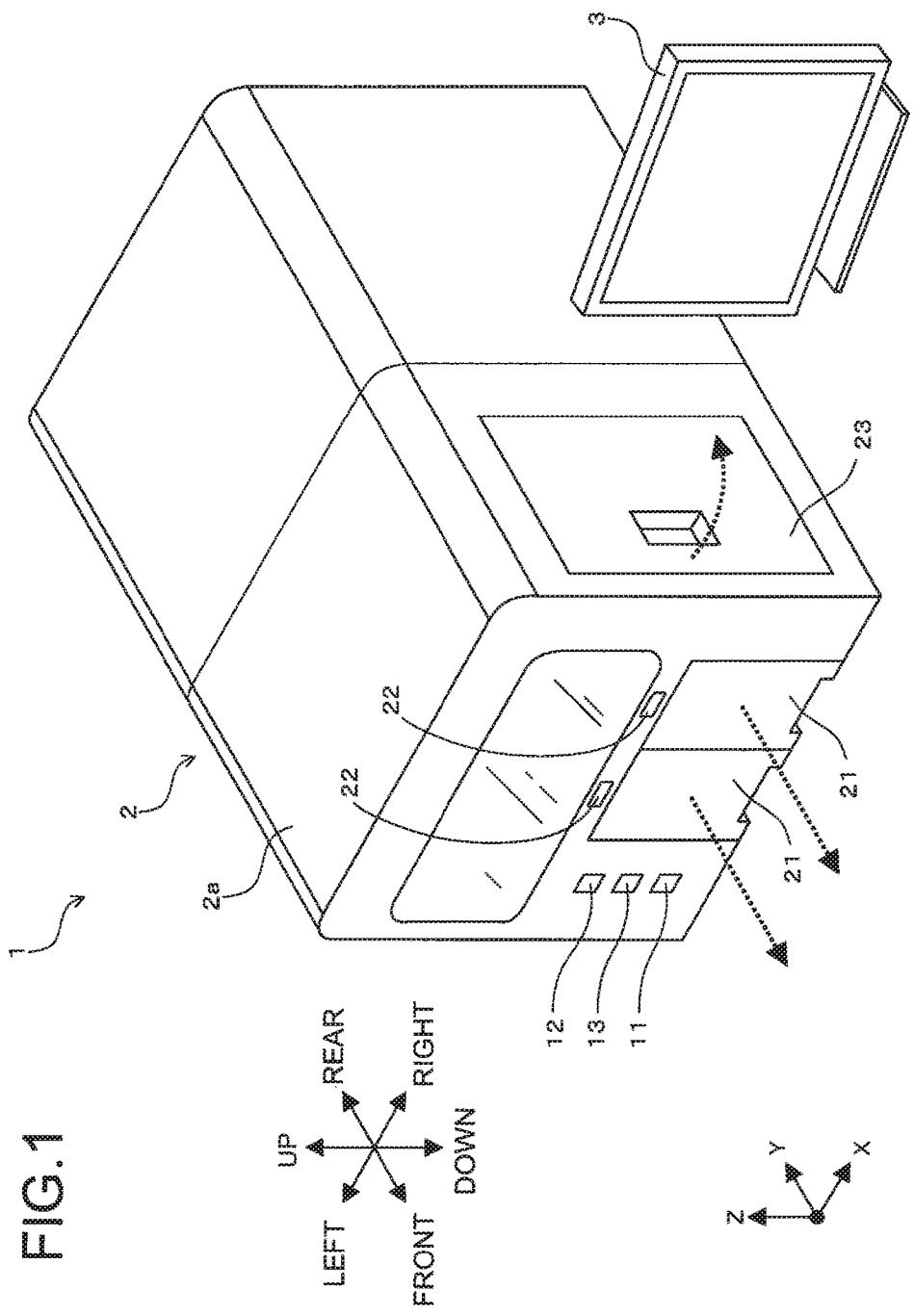
FIG. 1 is a schematic diagram illustrating an outside appearance of a sample analyzer according to an embodiment.

FIG. 1 is a diagram illustrating an outside appearance of sample analyzer 1 according to the embodiment.

Sample analyzer 1 includes main body 2 and display input unit 3, which is a touch panel display. Main body 2 is covered with case 2a and is provided with power button 11 configured to operate a power source of sample analyzer 1, start button 12, stop button 13, two panels 21, and two lamps 22 on the front side of case 2a. Drawers 30 (see, FIG. 2) are provided respectively on the back sides of two panels 21. Two lamps 22 indicate states of corresponding drawers 30. Openable/closable door 23 is provided on the front side of the right side surface of case 2a.

When continuously processing multiple samples (hereinafter, referred to as "sampler processing"), an operator pulls drawer 30 by pulling panel 21, sets a rack holding sample tubes into drawer 30, and then pushes start button 12. In addition, preferably, when processing one sample (hereinafter referred to as "manual processing"), the operator opens door 23 and sets sample tubes into tube set unit 71 (see, FIG. 2) inside case 2a and pushes start button 83 (see, FIG. 2) inside case 2a.

Figure 2:
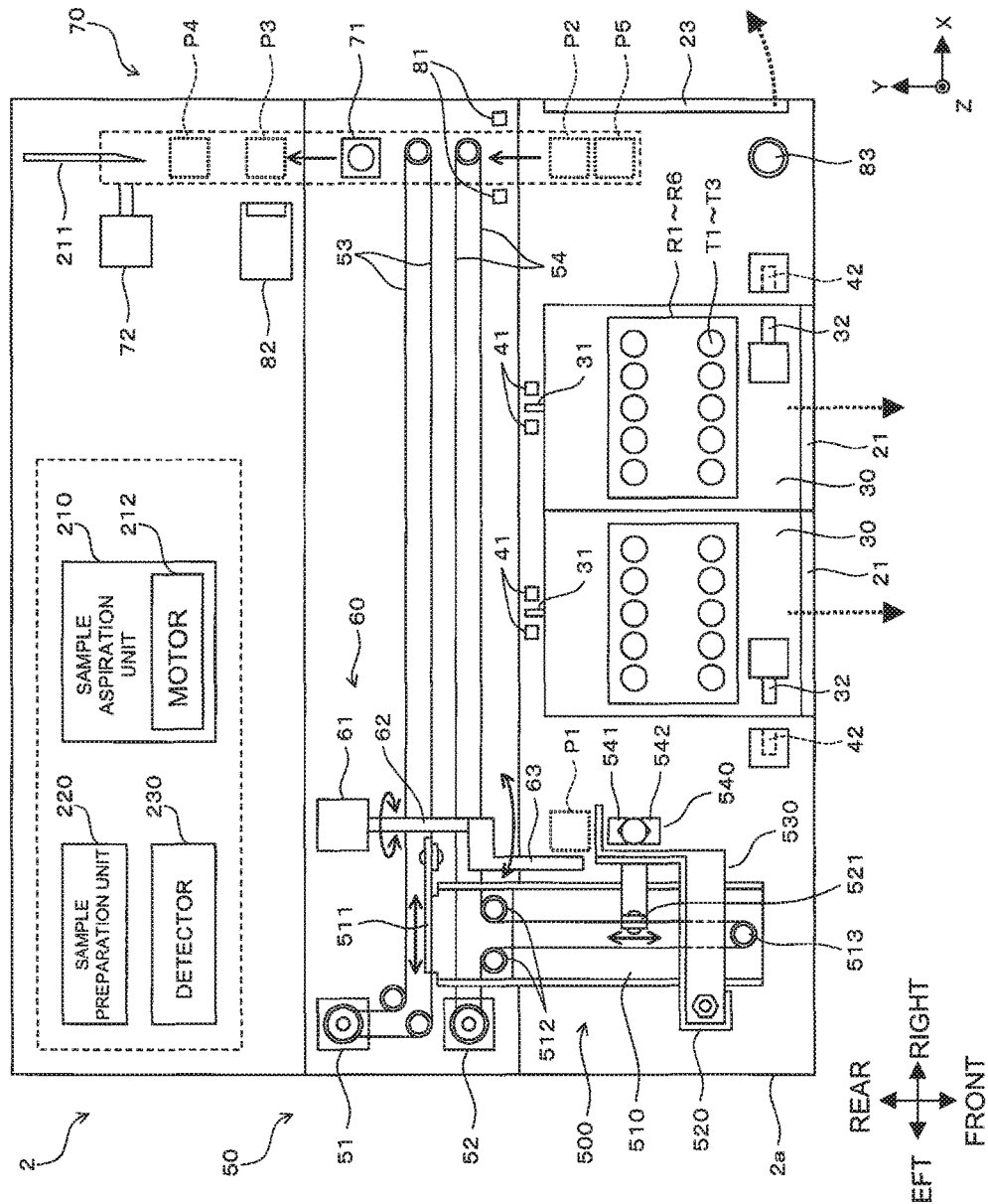
FIG. 2 is a schematic diagram illustrating a case where an inside of a case according to the embodiment is seen from above.

FIG. 2 is a schematic diagram illustrating a case where the inside of case 2a is seen from above.

Main body 2 includes two drawers 30 configured to set racks R1 to R6 (see, FIG. 3A), transmission sensors 41 configured to respectively detect two drawers 30 being set in case 2a in a closed state, holes 42 configured to respectively fix two drawers 30, tube transfer unit 50 configured to transfer sample tubes T1 to T3 (see, FIG. 3B), stirrer mechanism 60 configured to stir a sample by turning sample tubes T1 to T3 down, back-and-forth conveyance unit 70 configured to move sample tubes T1 to T3 in back and forth directions, transmission sensor 81 configured to detect whether or not a sample tube exists in back-and-forth conveyance unit 70, barcode reader 82, start button 83, sample aspiration unit 210 configured to aspirate samples in sample tubes T1 to T3, sample preparation unit 220, detector 230, and measurement samples.

Referring to FIGS. 3A to 5C, racks R1 to R6, sample tubes T1 to T3, and drawers 30 are described.

Figure 3B:
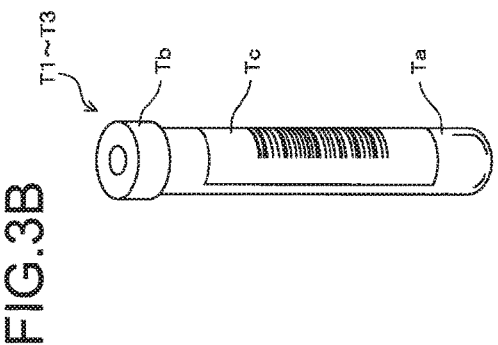
FIG. 3B is a diagram illustrating an outside appearance of a sample tube according to the embodiment.
Figure 3A:
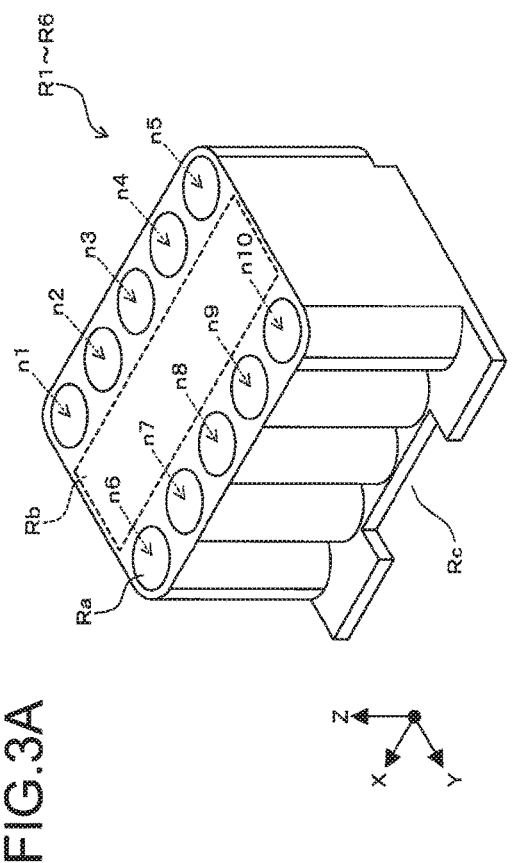
FIG. 3A is a perspective view illustrating a case where a rack according to the embodiment is seen from above.

FIG. 3A is a perspective diagram illustrating a case where racks R1 to R6 are seen from above. It is to be noted that in FIG. 3A, coordinate axes illustrated in FIG. 2, which is used when racks R1 to R6 are set in drawers 30 are also illustrated.

In the embodiment, as described later, six kinds of racks R1 to R6 are used according to kinds of sample tubes. As illustrated in FIG. 3A, shapes of racks R1 to R6 are exactly same with one another when seen from above but shapes thereof which are seen from bottom are different from one another. The shapes of racks R1 to R6 are described by referring to FIGS. 4A to 4F later.

To allow 10 sample tubes T1 to T3 to be held vertically, 10 holders Ra are formed in racks R1 to R6, and 10 holders Ra are formed so that each 5 holders Ra are arrayed in a double row in front and rear sides. As illustrated in FIG. 3A, positions of 10 holders Ra are referred to as holding position n1 to n10 for convenience. Also, the top surface of racks R1 to R6 are parallel with the X-Y plane, and intermediate portion Rb is formed between the row of holding positions n1 to n5 and the row of holding positions n6 to n10. In addition, dent portion Rc that dents inside the periphery thereof is formed on the rear side (the Y-axis positive side) of the lower end of rack R1 to R6.

FIG. 3B is a diagram illustrating an outer appearance of sample tubes T1 to T3.

Sample tubes T1 to T3 include body portion Ta, lid portion Tb, and barcode label Tc. Body portion Ta is a tubular container configured of translucent glass or synthetic resin and has an opening formed on an upper end thereof. Body portion Ta holds a sample and the opening in the upper end is tightly sealed with lid portion Tb. Lid portion Tb is configured to allow piercer 211 (see FIG. 2) to pass therethrough. Barcode label Tc includes a barcode including sample ID printed thereon. Barcode label Tc is adhered to the side surface of body portion ta.

Figure 3E:
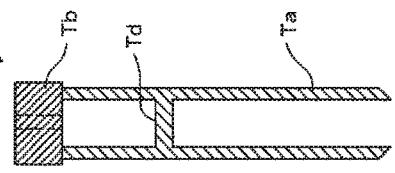
FIGS. 3C to 3E are cross-sectional diagrams of the sample tube according to the embodiment.
Figure 3D:
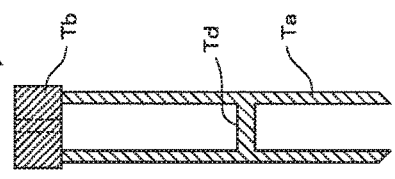
Figure 3C:
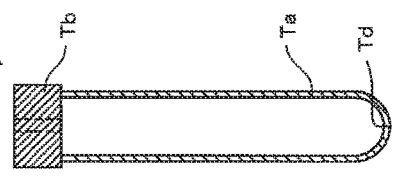

Each of FIGS. 3C and 3E is a cross-sectional diagram of sample tubes T1 to T3. For example, sample tubes T1 to T3 are used as blood-collecting vessels.

Bottom surface Td is formed on a lower end of an inner side of body portion Ta, and the positions of bottom surfaces Td of sample tubes T1 to T3 become higher in the order of sample tubes T1 to T3. Accordingly, volumes of samples containable in sample tubes T1 to T3 become smaller in the order of sample tubes T1 to T3.

Each of FIGS. 4A to 4F is a perspective diagram illustrating a case where racks R1 to R6 are seen from bottom (Z-axis negative side).

On the lower end of racks R1 to R6, in addition to recessed portion Rc illustrated in FIG. 3A, projection portion Rd which outwardly projects from the periphery thereof is formed on the opposite side of recessed portion Rc (the Y-axis negative side of the lower end of racks R1 to R6).

Also, on the lower surface of racks R1 to R6, projection portion Re is formed. A lower end of projection portion Re is positioned higher than the lower end of racks R1 to R6. There are three portions where projection portion Re is to be formed, and projection portion Re is formed in at least one position among these positions. Specifically, projection portion Re is formed in each of the three positions in rack R1, and projection portions Re are formed in the center and a position on the X-axis positive side in rack R2, projection portions Re are formed in positions on the X-axis positive side and the X-axis negative side in rack R3. In addition, projection portions Re are formed in the center and a position on the X-axis negative side in rack R4, and projection portion Re is formed in the center in rack R5, and projection portion Re is formed in a position on the X-axis negative side.

Here, samples according to the embodiment include regular samples whose analysis is not particularly in harry (hereinafter, referred to as "regular sample") and samples whose analysis has to be performed preferentially to the regular samples (hereinafter, referred to as "priority sample"). Also, three kinds of above-described sample tubes T1 to T3 are used as sample tubes, and any one of the regular samples and the priority samples is held in each of the sample tubes T1 to T3. Accordingly, in the present embodiment, there are sample tubes T1 to T3 holding the regular samples, and sample tubes T1 to T3 holding the priority samples. As a result, there are six kinds of sample tubes in combination.

Also, in the embodiment, a rack to be used is determined for each of the six kinds of the sample tubes. Sample tubes T1 to T3 holding regular samples are set only in racks R1 to R3, respectively, and sample tubes T1 to T3 holding priority samples are set only in racks R4 to R6, respectively. Hereinafter, racks R1 to R3 are collectively referred to as a "regular rack" and racks R4 to R6 are collectively referred to as a "priority rack." In this manner, racks R1 to R6 in which sample tubes T1 to T3 are set according to the above rules are set in drawer 30 which is pulled out forwardly by an operator.

Figure 5A:
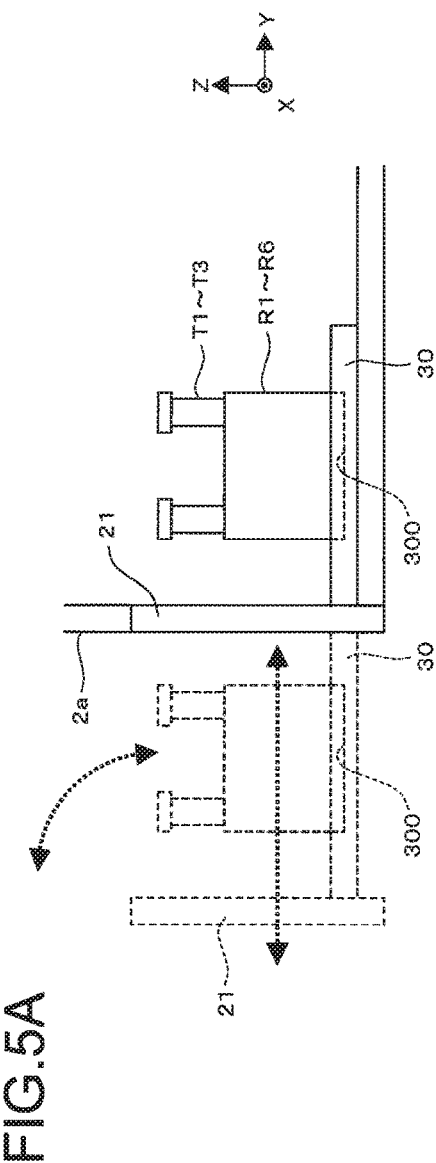
FIG. 5A is a schematic diagram illustrating forward and backward movements of a drawer according to the embodiment.

FIG. 5A is a schematic diagram illustrating the back and forth movements of drawer 30.

Panel 21 is connected with a front end (end portion on the Y-axis negative side) of drawer 30, which is moved back and forth along the panel 21 when an operator moves panel 21 back and forth. Also, rack set unit 300 is formed in drawer 30 for installing racks R1 to R6. When drawer 30 is moved back and forth, rack set unit 300 is also moved between a loaded position in which the rack is loaded in case 2a and a drawn position in which the rack is drawn out from case 2a.

When drawer 30 is drawn out and rack set unit 300 is positioned in the drawn position, the operator may set the rack in rack set unit 300 and may also take out the rack set in rack set unit 300. Also, when rack set unit 300 is positioned in the loaded position, processing is performed with mechanisms inside case 2a on the sample tubes held in the rack set in rack set unit 300.

Figure 5C:
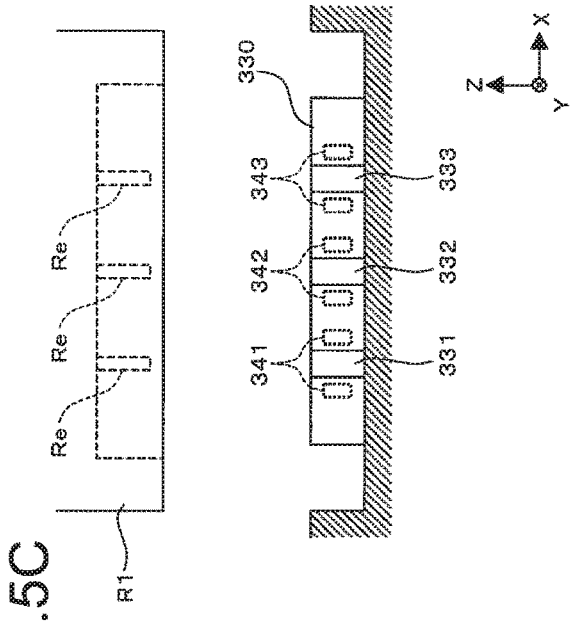
FIG. 5C is a diagram illustrating a case where a cut-apart rack set unit is seen from the front thereof.
Figure 5B:
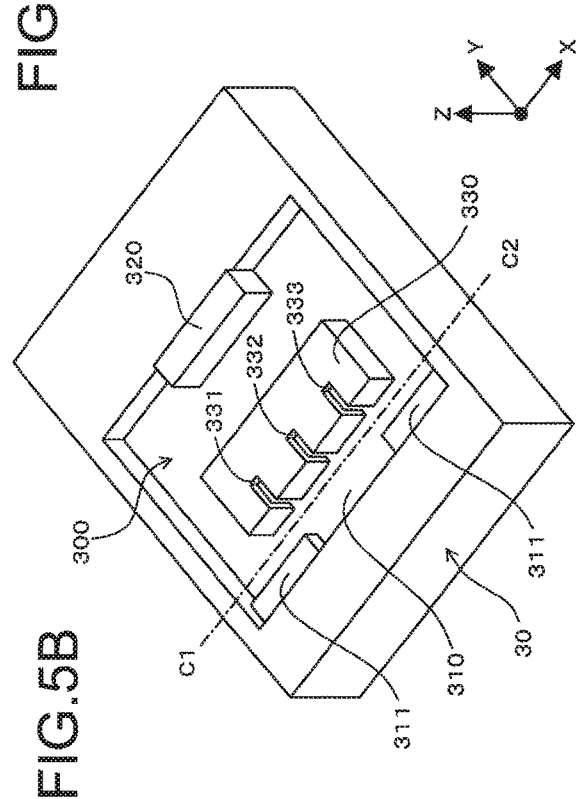
FIG. 5B is a diagram illustrating a configuration of the drawer according to the embodiment.

FIG. 5B is a diagram illustrating the configuration of drawer 30. Here, for convenience's sake, FIG. 5B omits illustration of flange portion 31 and bar member 32 (see FIG. 2), which are to be described later.

Rack set unit 300 is formed in a position near the center of drawer 30, and the bottom surface of rack set unit 300 is formed so as to be lower by one step than the upper surface of drawer 30. In the front end and rear end of rack set unit 300, dent portion 310 and projection portion 320 are formed so as to respectively engage with projection portion Rd and dent portion Rc of the rack set in rack set unit 300. The upper surfaces of projection portions 311 to the right and left of dent portion 310 are lower than the upper surface of drawer 30, and the upper surface of projection portion 320 is higher than the upper surface of drawer 30. Also, projection portion 330 is formed in the center of rack set unit 300. Gaps 331 to 333 corresponding to three projection portions Re of the rack set in rack set unit 300 are formed in projection portion 330.

FIG. 5C is a diagram illustrating the case where rack set unit 300 taken out by C1-C2 in FIG. 5B is seen from front thereof (in the Y-axis positive direction).

In projection portion 330, transmission sensors 341 to 343 are provided to sandwich gaps 331 to 333 therebetween. For example, when rack R1 is set in rack set unit 300, three projection portions Re formed in rack R1 are positioned in gaps 331 to 333. Accordingly, when it is detected by detection signals of sensors 341 to 343 that projection portion Re is positioned in at least one of gaps 331 to 333, it is recognized that the rack is set in rack set unit 300. Also, hard disk 270 (see, FIG. 9) in main body 2 stores the configuration of projection portion Re of racks R1 to R6 illustrated in FIGS. 4A to 4F. With this, the rack set in rack set unit 300 may be identified as one of racks R1 to R6.

Also, when the rack is placed in rack set unit 300 so as to reverse the back and forth directions, the bottom surface of the rack including projection portion Rd and dent portion Rc comes in contact with projection portions 311, 320, which causes the rack to tilt in the back and forth directions. Accordingly, the operator may realize that the placement direction of the rack is wrong. It is to be noted in the embodiment that even when the rack is placed so as to reverse the back and forth directions, projection portion Re and rack set unit 300 are configured so as not to bring projection portion Re into contact with projection portion 330.

Return to FIG. 2. When a rack is set in drawer 30 and drawer 30 is pushed to the rear side thereof, flange portion 31 provided on the rear side of drawer 30 is positioned in a gap between transmission sensors 41 provided inside case 2a. Accordingly, it is detected based on detection signals of sensors 41 that drawer 30 is drawn out and drawer 30 is closed. When transfer of sample tubes is started on the rack set in drawer 30 by tube transfer unit 50 after the rack is set in drawer 30 and this drawer 30 is closed, drawer 30 is locked so that the rack is not forwardly pulled out by accident. Specifically, bar member 32 provided in drawer 30 is driven by an unillustrated driver in the Y-axis direction and is inserted into hole 42 provided inside case 2a, so that drawer 30 is limited to be forwardly pulled out. Also, bar member 32 is driven in a direction opposite to the direction in which it is locked, so that the lock of drawer 30 is released so that drawer 30 can be forwardly pulled out.

FIG. 7A is a flowchart illustrating lock processing on drawer 30. This processing is performed by CPU 201 to be described later.

Grippers 541, 542 (see, FIG. 2) of tube transfer unit 50 start moving from an initial position on the left-rear side thereof inside case 2 and a transfer operation of sample tubes on the rack set in drawer 30 is started (S101: YES), drawer 30 is locked (S102).

Subsequently, the sample tubes held by the rack are sequentially taken out by tube transfer unit 50 from the rack and transferred. Then, as is described later, stirring processing and aspiration processing are performed on samples held in the taken-out sample tubes. When the processing is terminated on the samples, the sample tubes are returned to the original holding positions of the original rack. In this manner, when the processing is terminated on all the samples on the rack (S103: YES), the processing stands by until grippers 541, 542 of tube transfer unit 50 retracts to the position where the grippers do not come in contact with drawer 30 which is forwardly pulled out (S104). When grippers 541, 542 are retracted (S104: YES), the lock of this drawer 30 is released (S105). In this manner, the lock processing on drawer 30 is terminated.

Return to FIG. 2. Tube transfer unit 50 includes motors 51, 52, belts 53, 54, and movement body 500.

Movement body 500 includes right-left movement unit 510, front-back movement unit 520, up-down movement unit 530, and holder 540. Right-left movement unit 510 is movable in the right and left directions while being supported by a guide (unillustrated), which is provided in case 2a and extends in the right and left directions. Front-back movement unit 520 is movable in the back and forth directions while being supported by a guide (unillustrated) which is provided in right-left movement unit 510 and extends in the back and forth directions. Up-down movement unit 530 is moved relative to front-back movement unit 520 in the up and down directions by a cylinder (unillustrated) provided in front-back movement unit 520. Holders 540 are configured to be capable of holding sample tubes T1 to T3 between the back and forth directions, and are supported by up-down movement unit 530 to be rotatable about the Y-axis as a rotation axis.

Motor 51 drives belt 53 installed around pulleys provided on the right and left sides of case 2a in the right and left directions. Attachment stay 511 of right-left movement unit 510 is fixed in the belt 53. Accordingly, the right-left movement unit 510 becomes movable in the right and left directions along with the belt 53. Motor 52 drives belt 54 installed in pulleys provided on the right and left sides of case 2a in the right and left directions. One portion of belt 54 is forwardly folded by pulleys 512 provided in right-left movement unit 510 and is installed on the pulleys 513 provided in the front side of right-left movement unit 510. Attachment stay 521 of front-back movement unit 520 is fixed in belt 54 between pulleys 512, 513. Accordingly, front-back movement unit 520 becomes movable in the back and forth directions along with belt 54. Thus, holders 540 become freely movable in the X, Y, and Z directions in case 2a.

Stirrer mechanism 60 includes motor 61, shaft 62 which is connected with motor 61 and extends in the Y-axis direction, and abutting member 63 fixed in shaft 62. The sample tube, which is held by grippers 541, 542 and is positioned in position P1 is pushed by abutting member 63 and is turned down, so that a sample inside the sample tube is stirred.

FIGS. 6A and 6B schematic diagrams, each illustrating the case where up-down movement unit 530, holder 540, and stirrer mechanism 60 are seen in the X-axis direction.

Up-down movement unit 530 includes base board 531, shaft 532 fixed to base board 531, cylinder 533 fixed to base board 531, plate member 534 provided in an end portion on the Y-axis negative side of rod 533a of cylinder 533, flange portion 534a provided in an upper end of plate member 534, and transmission sensors 535 provided in base board 531 on the Y-axis positive side of flange portion 534a.

Holder 540 includes grippers 541, 542 provided in shaft 532 to be rotatable about shaft 532 as a rotation axis, and spring 543 provided between grippers 541, 542. Gripper 541 is provided in shaft 532 so as not to move in the Y-axis direction, and the upper end of gripper 542 is positioned on the Y-axis negative side of plate member 534.

When force is not added to rod 533a in the Y-axis negative direction, gripper 542 is pulled in the Y-axis positive direction with contractile force of spring 543 and the lower ends of grippers 541, 542 come in contact with each other. At this time, plate member 534 is pushed in the Y-axis positive direction by the upper end of gripper 542 and flange portion 534a is positioned in the gap between sensors 535. Accordingly, it is detected that the lower ends of grippers 541, 542 come in contact with each other, that is, the sample tube is not gripped by holder 540.

When cylinder 533 pushes rod 533a in the Y-axis negative direction, as illustrated in FIG. 6A, plate member 534 moves in the Y-axis negative direction. At this time, plate member 534 pushes the upper end of gripper 542 in the Y-axis negative direction with contractile force of spring 543, and flange portion 534a moves in the Y-axis negative direction of sensor 535.

In order for grippers 541, 542 to grip sample tubes T1 to T3, grippers 541, 542 are firstly moved to the position of the sample tube (rack holding position) to be gripped in a state where grippers 541, 542 are opened, and lowered to a position at a predetermined height as illustrated in FIG. 6A. Then, when the force of cylinder 533 to push rod 533a is weakened, gripper 542 moves in the Y-axis positive direction, and body portion Ta of the sample tube is gripped by grippers 541, 542 with the contractile force of spring 543 as illustrated in FIG. 6B. Since the sample tube is between grippers 541, 542 at that time, gripper 542 stops at a predetermined position and flange portion 534a is not positioned in the gap between sensors 535. Accordingly, it is detected that the holder 540 grips the sample tube.

Accordingly, in an operation where grippers 541, 542 perform a gripping operation on each holding position of the rack, it can be detected that the sample tube is not held in this holding position if flange portion 534a is positioned in the gap between sensors 535, whereas it can be detected that the sample tube is in this holding position if flange portion 534a is positioned outside the gap between sensors 535. Then, when it is detected that the sample tube is not held in the gripping operation, the transfer operation of the sample tube to this holding position is stopped.

FIG. 7B is a flowchart illustrating the transfer processing on the sample tubes. This processing is performed by CPU 201 to be described later.

When the transfer operation of tube transfer unit 50 is started, grippers 541, 542 of tube transfer unit 50 are moved to a target holding position (S201), and the gripping operation is executed on the holding positions (S202). At this time, as described above, it is detected that the sample tube is in the holding position. When the sample tube is in the holding position (S203: YES), grippers 541, 542 of tube transfer unit 50 execute the transfer operation on the sample tube (S204). On the other hand, when the sample tube is not in the holding positions (S204: NO), the transfer operation is not performed.

In this manner, the processes of S201 to S205 are repeatedly carried out until the processing is terminated on all the samples in the rack (S205). When the processing is terminated on all the samples in the rack (S205: YES), grippers 541, 542 of tube transfer unit 50 are returned to the initial position (S206), and the transfer processing is terminated.

Return to FIGS. 6A and 6B. The sample tube taken out from the rack is transferred by tube transfer unit 50 to position P1 illustrated in FIG. 2, and the sample tube is turned down by stirrer mechanism 60 in position P1. Specifically, when shaft 62 is rotated by motor 61, the front end of abutting member 63 moves along with an arch using shaft 62 as the center thereof in the X-Z plane. Accordingly, body portion Ta of the sample tube pushed by abutting member 63 from the X-axis negative side. When the sample tube is returned to the vertical state, shaft 62 is reversely rotated by motor 61 and abutting member 63 is separated from the sample tube. Accordingly, grippers 541, 542 gripping the sample tube are returned to the vertical state with the weight thereof.

Here, abutting member 63 pushes the sample tube from the X-axis negative side, and thus tube transfer unit 50 has to position the sample tube on the X-axis positive side of abutting member 63. Also, in the stirring processing, since the sample tube is turned down in the X-direction, space extending in the X-axis direction is needed. For this reason, in the embodiment, stirrer mechanism 60 and position P1 are provided on the rear-left of the racks set in two drawers 30 when two drawers 30 are closed.

Return to FIG. 2. When stirring processing by stirrer mechanism 60 is terminated in position P1, this sample tube is set by tube transfer unit 50 in tube set unit 71 of back-and-forth conveyance unit 70 positioned in position P2. Back-and-forth conveyance unit 70 includes tube set unit 71 which is capable of holding the sample tube and motor 72 to move tube set unit 71 in the back and forth directions.

The sample tube set in tube set unit 71 in position P2 is conveyed to position P3 by tube set unit 71. When the sample tube is positioned in position P3, barcode reader 82 provided near position P3 reads sample ID from barcode label Tc adhered to the sample tube. Then, the sample tube is conveyed to position P4 by tube set unit 71. When the sample tube is positioned in position P4, a predetermined amount of sample is aspirated by sample aspiration unit 210 from the sample tube via piercer 211. Sample aspiration unit 210 includes piercer 211 to aspiration the sample in the sample tube and motor 212 with a stepping motor to drive piercer 211 in the up and down directions.

When aspiration of the sample is terminated, this sample tube is conveyed to the front of tube set unit 71 and is positioned in position P2. Then, this sample tube is returned to the original rack holding position by tube transfer unit 50. In this manner, the sample tubes held in the rack are sequentially taken out and sample aspiration unit 210 aspirations the sample.

The sample aspirated through piercer 211 is discharged to sample preparation unit 220. Sample preparation unit 220 mixes the sample with a reagent and the mixed solution is heated to prepare a measurement sample. The prepared measurement sample is supplied to detector 230. Detector 230 acquires various kinds of signals by emitting laser beams to the measurement sample. The acquired measurement result is analyzed by CPU 201 (see, FIG. 9) and the analysis result is displayed in display input unit 3.

When the analysis of one sample is preferentially performed (in the case of the manual processing), the operator stirs the sample in the sample tube in advance. The operator opens door 23 and sets this sample tube in tube set unit 71 positioned in position P5 (see, FIG. 2), and then pushes start button 83. This sample tube is conveyed to the back of tube set unit 71. Then, barcode reader 82 reads sample ID, and the sample is aspirated. After that, this sample tube is positioned by tube set unit 71 in position P5, and the operator opens door 23 to take out the sample tube from case 2a.

It is to be noted that tube set unit 71 is positioned in position P5 when processing on the two racks is not performed, and is positioned in position P2 when processing on any one of the two racks is performed. Accordingly, the manual processing can be executed when processing is not performed on both two racks. When the manual processing is performed when processing on any one of the two racks is performed, the operator opens door 23 and sets the sample tube holding a priority sample in tube set unit 71 positioned in position P5 after an operation of suspending the processing on the rack is performed, and presses start button 83.

Here, since piercer 211 is consumables and has to be regularly replaced by a serviceman. The serviceman replaces piercer 211 from the right surface of main body 2 in replacement. Also, tube set unit 71 moves between position P5 where the sample tube is directly set by the operator and position P4 where aspiration is performed by piercer 211 in the back and forth directions. For this reason, in the embodiment, tube set unit 71 is provided on the right end in main body 2 for the sake of convenience of the operator and serviceman. Also, position P2 where the sample tube is set by tube transfer unit 50 is provided in the right direction of position P1 so that a distance from position P1 becomes the shortest and on the rear right side of the rack set in two drawers 30 when two drawers 30 are closed.

FIG. 8A is a diagram illustrating stirring processing by stirrer mechanism 60. FIGS. 8B to 8D are diagram, each illustrating the aspiration processing by sample aspiration unit 210. FIG. 8E is a conceptual diagram illustrating a setting table configuration stored in hard disk 270 (see, FIG. 9) in main body 2.

Refer to FIG. 8A. When a turned-down operation in which a sample tube is returned from the vertical state to the vertical state after the turned-down state is counted as one, the numbers of turning down the sample tubes T1 to T3 are respectively set to fn1, fn1, and fn2 as indicated in the setting table in FIG. 8E. Here, fn1<fn2. Accordingly, the sample in sample tube T3 whose capacity is smaller than those of sample tubes T1 and T2 can be sufficiently stirred.

Now refer to FIGS. 8B to 8D. In order to lower piercer 211 to the sample tube, the lower end of piercer 211 is aligned with the initial position, and then motor 212 is given a predetermined number of pulses and accordingly lowers piercer 211. In this process, the number of pulses given to motor 212 is set to pn1, pn2, and pn3 for sample tubes T1 to T3, respectively, as indicated in the setting table in FIG. 8E so that a lowering amount becomes suitable. Here, pn1>pn2>pn3. Accordingly, piercer 211 can be properly lowered according to the height of bottom surfaces Td of sample tubes T1 to T3.

Figure 9:
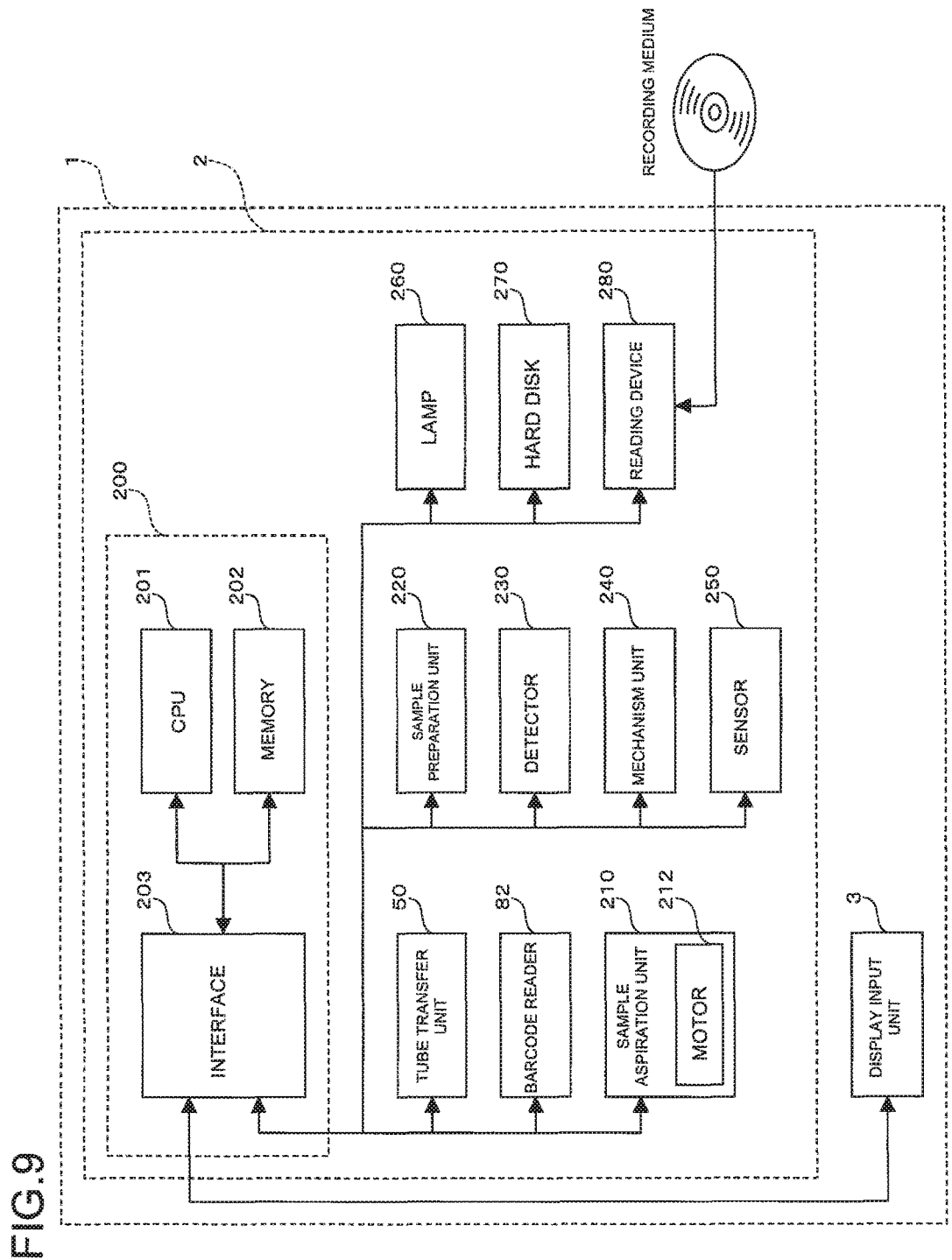
FIG. 9 is a block diagram illustrating a configuration of a sample analyzer according to the embodiment.

FIG. 9 is a block diagram illustrating the configuration of sample analyzer 1.

Main body 2 includes substrate 200, mechanism unit 240, sensor unit 250, lamp unit 260, hard disk 270, and read device 280 in addition to above-described tube transfer unit 50, barcode reader 82, sample aspiration unit 210, sample preparation unit 220, and detector 230. Substrate 200 includes CPU 201, memory 202, and interface 203.

CPU 201 executes computer programs stored in memory 202, computer programs loaded in memory 202, and processing illustrated in FIGS. 7A and 7B. CPU 201 controls the units of main body 2 and display input unit 3 and receives signals from the units of main body 2 and display input unit 3, through interface 203.

Mechanism unit 240 includes a mechanism to drive the units of main body 2. Sensor unit 250 includes a sensor to detect that door 23 is closed and a sensor to detect that power button 11, start buttons 12, 83, or stop button 13 is pressed, in addition to above-described two sensors 41, 81 and 341 to 343, 535. Lamp unit 260 includes two lamps 22.

Hard disk 270 stores an operating system, computer programs which are executed by CPU 201, the configuration of projection portions Re of racks R1 to R6, and the setting table in FIG. 8E. Read device 280 includes a CD drive, DVD drive, or the like, and can read out computer programs and data, which are stored in the recording medium.

Figure 10A:
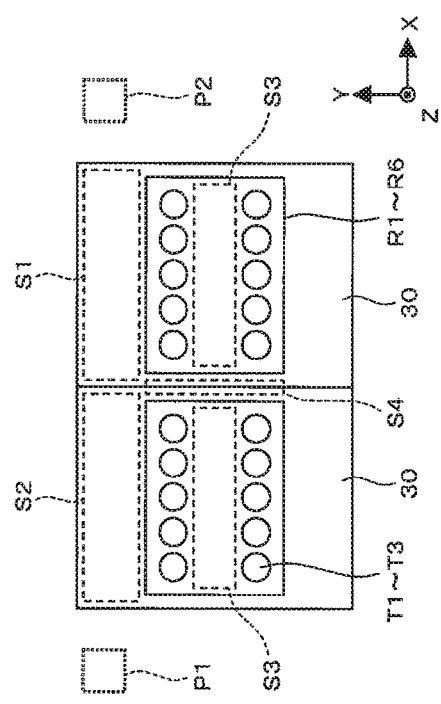
FIG. 10A is a schematic diagram illustrating a case where a portion near two drawers according to the embodiment is seen from above.

FIG. 10A is a schematic diagram illustrating the case where a portion near two drawers 30 is seen from above.

In the embodiment, as described above, positions P1 and P2 are respectively provided in the rear left side and the rear right side of the racks set in two drawers 30. Also, the units of main body 2 are configured so that space S1 is provided to the rear of the rack set in the right drawer 30 and space S2 is provided to the rear of the rack set in the left drawer 30. Also, center portion Rb provided in the rack (see, FIG. 3A) forms space S3 between the row of holding positions n1 to n5 and the row of holding positions n6 to n10. The width of center portion Rb in the back and forth directions is set slightly larger than the diameter of body portion Ta of the sample tube. Also, space S4 is formed between the racks set in right and left drawers 30. Spaces S1, S2, and S4 are spaces extending above drawers 30 in areas illustrated by the broken lines in the plan view of FIG. 10A, and are configured to be small to an extent that tube transfer unit 50 can just transfer the sample tube. Space S3 is a space extending above center portion Rb in the area illustrated by the broken line in the plan view of FIG. 10A.

It is to be noted that right drawer 30 and left drawer 30 respectively correspond to a "first drawer" and a "second drawer" described in claims.

Figure 11A:
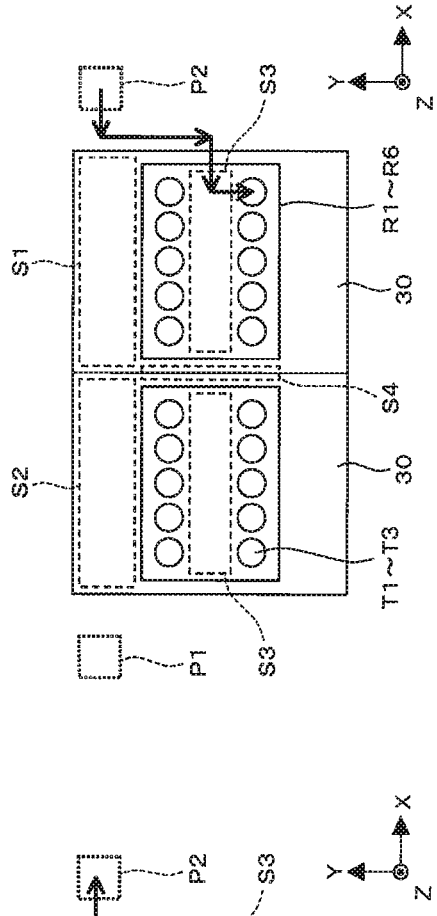
FIGS. 11A to 11D are diagrams, each illustrating a path in which sample tubes held in a right rack according to the embodiment are transferred by the tube transfer unit.
Figure 11B:
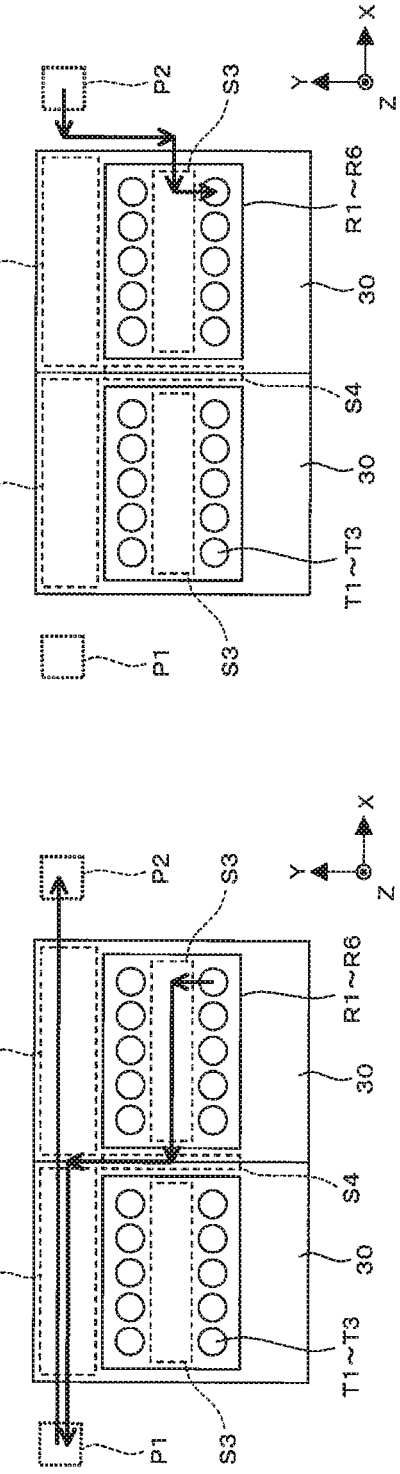

FIGS. 11A and 11B are diagrams, each illustrating a path in which the sample tube held in holding position n1 in the right rack is transferred by tube transfer unit 50.

Refer to FIG. 11A. When the sample tube held in position n1 in the right rack is picked out of the rack by being gripped by grippers 541, 542, the sample tube is transferred slightly backwardly to be positioned in space S3. Subsequently, the sample tube is transferred to the left in space S3 to be positioned in space S4, and is backwardly transferred in space S4 to be positioned in a position covering spaces S1, S2. After that, this sample tube is transferred to the left in space S2 to be positioned in position P1. Stirring processing is performed in position P1 and then the sample tube is transferred to the right in space S2 and space S1 to be set in tube set unit 71 positioned in position P2.

Refer to FIG. 11B. When the sample tube positioned in position P2 after being conveyed from the rear side by tube set unit 71 is picked out of tube set unit 71 by being gripped by grippers 541, 542, the sample tube is returned to original holding position n1 after passing the right space of the right rack and space S3. Similarly, the sample tubes held in holding positions n2 to n5 of the right rack are also transferred as illustrated in FIGS. 11A and 11B.

Figure 11C:
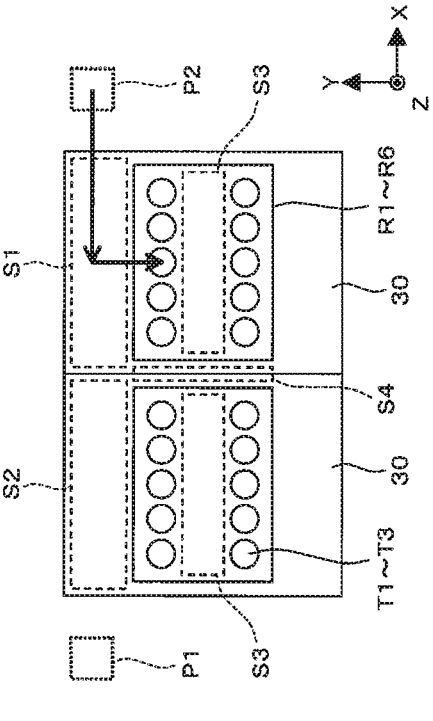
Figure 11D:
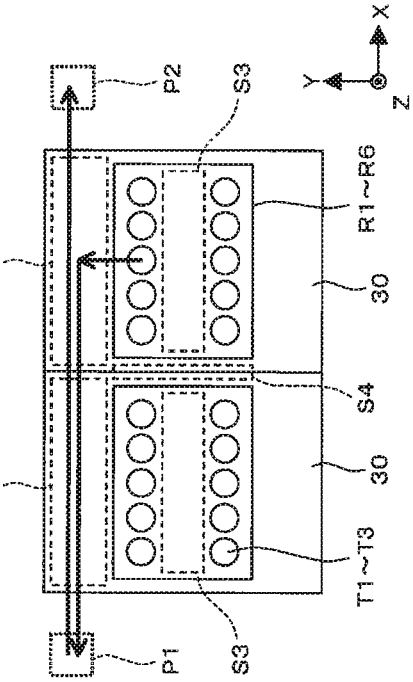

The sample tubes held in the rear row (holding positions n6 to n10) of the right rack are transferred to the right and left in spaces S1, S2 as illustrated in FIGS. 11C and 11D.

FIGS. 12A and 12B are diagrams, each illustrating a path in which the sample tube held in holding position n1 of the left rack is transferred by tube transfer unit 50.

Refer to FIG. 12A. When the sample tube held in position n1 in the left rack is picked out of the rack by being gripped by grippers 541, 542, the sample tube is firstly transferred slightly backwardly to be positioned in space S3 and then is transferred to the left in space S3 to be positioned in the left side of the space of the rack. After that, this sample tube is positioned in position P1 after passing the left side of the left rack. Stirring processing is performed in position P1 and then the sample tube is transferred to the right in space S2 and space S1 to be set in tube set unit 71 positioned in position P2.

Refer to FIG. 12B. When the sample tube positioned in position P2 after being conveyed from the rear side by tube set unit 71 is picked out of tube set unit 71 by being gripped by grippers 541, 542, the sample tube is transferred to the left in space S1 to be positioned in space S4. Then, this sample tube is transferred to the left in space S3 to be returned to original holding position n1. Similarly, the sample tubes held in holding positions n2 to n5 of the left rack are also transferred as illustrated in FIGS. 12A and 12B.

It is to be noted that the sample tubes held in the rear row (holding positions n6 to n10) of the left rack are transferred to the right and left in spaces S1, S2 as illustrated in FIGS. 12C and 12D.

Figure 10B:
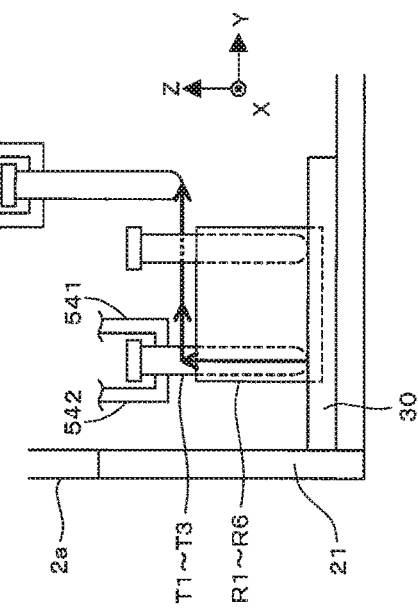
FIG. 10B is a diagram illustrating a path seen in the X-axis direction in which sample tubes held in the front row of a rack according to the embodiment are transferred by a tube transfer unit.
Figure 10C:
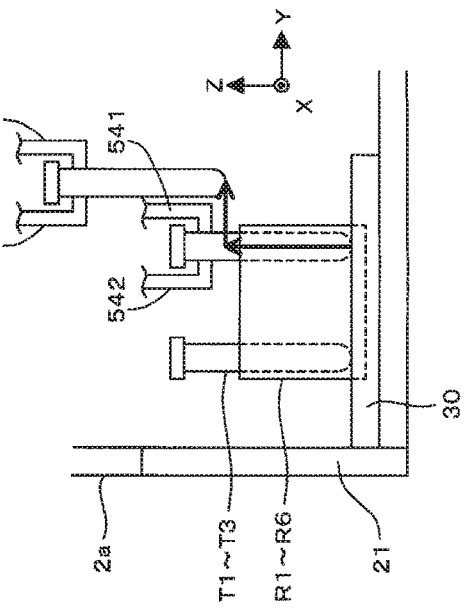
FIG. 10C is a diagram illustrating a path seen in the X-axis direction in which sample tubes held in the rear row of the rack according to the embodiment are transferred by the tube transfer unit.

FIGS. 10B and 10C are diagrams, each illustrating a case where a path in which the sample tubes held in the front row (holding positions n1 to n5) or rear row (holding positions n6 to n10) of the rack are transferred by tube transfer unit 50 is seen from the X-axis negative direction. It is to be noted that the thick arrows indicate a path of the lower end of the sample tube.

Refer to FIG. 10B. The sample tube held in the front row is picked out so that the lower end thereof is positioned slightly higher than the upper surface of the rack. Subsequently, this sample tube is slightly transferred in the Y-axis positive direction, and is transferred in the X-axis direction after passing space S3 (see, FIG. 10A) between the front row and the rear row, and then is transferred to the rear side after passing space S4 or the left space of the rack. Refer to FIG. 10C. Similarly, the sample tube held in the rear row is picked out so that the lower end thereof is positioned slightly higher than the upper surface of the rack. Subsequently, this sample tube is transferred slightly in the Y-axis positive direction. In this manner, the sample tube is transferred through a position at which the lower end of the sample tube is slightly above the upper surface of the rack, that is, at a height level at which the lower end of the sample tube travels near the upper surface of the rack, and the sample tube is not lifted to a level much higher than that. In other words, the transfer path set as described above enables the sample tube to be smoothly carried without lifting the sample tube largely.

Also, in the embodiment, when a rack is not set in drawer 30, lamp 22 above this drawer 30 is lit in green, and the lock of this drawer 30 is released. In addition, when a rack is set in drawer 30 but processing on the rack is not started yet, lamp 22 above this drawer 30 is also lit in green and the lock of this drawer 30 is released. Also, when processing on the rack set in drawer 30 is started and transferring the sample tube in the rack is started, lamp 22 above this drawer 30 flashes in green and this drawer 30 is locked. Also, when the processing on all the racks set in drawer 30 is terminated, lamp 22 above drawer 30 is lit off and the lock of drawer 30 is released.

It is to be noted that as illustrated in FIG. 7C, lighting processing of lamp 22 is controlled by CPU 201. This lighting processing is performed so that lamp 22 becomes the state illustrated on the right row in FIG. 2C when the state of drawer 30 is in the state illustrated in the left row in FIG. 7C.

As described above, in the embodiment, corresponding drawer 30 is forwardly pulled and the rack can be set in this drawer 30 when lamp 22 is lit in green and is lit off, and is not forwardly pulled and this drawer 30 cannot be set when lamp 22 flashes in green. Accordingly, it can be seen that an operator can see whether or not a rack can be set in corresponding drawer 30 by checking the state of lamp 22.

As described above, in the embodiment, as illustrated in FIGS. 12A and 12D, the sample tube held in the left rack is transferred passing space S1 on the rear side of the right rack without passing the front side of the right rack when the sample tube is positioned in position P2. Accordingly, even when the sample tube is being transferred from the left rack to position P2, the right rack can be forwardly pulled from main body 2. Thus, the sample tube can be efficiently replaced.

Also, the sample tube which is transferred from the left rack to position P2 is positioned in a place where the lower end thereof is slightly higher than the upper surface of the rack. In other words, the sample tube is transferred in a height in which the lower end thereof comes near the upper surface of the rack and is not lifted higher than this. For this reason, the sample tube being transferred from the left rack does not have to be lifted to a level higher than the upper end of the sample tube held in the right rack in order to avoid contact with the sample tube of the right rack when the right rack is pulled out. This can avoid increasing the size of the outer shape of sample analyzer 1 in the height direction.

As described above, sample tubes T1 to T3 used in the embodiment are used as blood-collecting tubes, for example. As illustrated in FIGS. 3C to 3E, they have an elongate shape. For this reason, when a sample tube is picked out of a rack and transferred, the lower portion of the sample tube to be transferred may cause interference on the upper portion of other sample tubes. This problem can be solved by largely lifting the sample tube so that the lower portion of the sample tube to be transferred becomes higher than the upper portion of other sample tubes. However, in this case, a large stroke to lift a sample tube needs to be provided inside sample analyzer 1, which causes an increase in the size of sample analyzer 1 in the height direction. For this reason, to solve the above problem and to suppress the increase in the size of sample analyzer 1 in the height direction, the transfer path of the sample tube has to be devised. In the embodiment, the transfer path of the sample tube set as described above enables avoidance of increase in the outer shape of sample analyzer 1 in the height direction, and smooth transfer of the sample tube.

Also, in the embodiment, as illustrated in FIGS. 11A to 11D, the sample tube held in the right rack is transferred passing space S2 on the rear side of the left rack without passing the front side of the left rack when the sample tube is positioned in position P1 where is a stirring position by stirrer mechanism 60. Accordingly, even when the sample tube is being transferred from the right rack to position P1, the left rack can be forwardly pulled from main body 2. Thus, the sample tube can be efficiently replaced. Also, since there is no need to lift the sample tube to a level higher than the upper end of the sample tube held by the left rack when the sample tube is being transferred from the right rack to position P1, the increase in the outer shape of sample analyzer 1 in the height direction can be avoided.

Also, in the embodiment, right and left drawers 30 include rack set unit 300, and a rack is detachably attachable to rack set unit 300. Accordingly, the sample tubes can be replaced all together at once, and thus the sample tube can be further efficiently replaced.

Also, in the embodiment, the rack has the configuration in which five holding portions Ra are arranged in two rows, so that the shape of the rack can be compact in the plan view. As a result, the shape of sample analyzer 1 can be compact. Also, center portion Rb is formed between the row of holding portions Ra in holding positions n1 to n5 and the row of holding portions Ra in holding positions n6 to n10, and space S3 formed by center portion Rb is used as a transfer space for the sample tubes. Accordingly, the transfer operation can be smoothly achieved.

Also, in the embodiment, space S4 formed between the racks set in the left and right drawers 30 is used as a transfer space for the sample tubes. Accordingly, the transfer operation can be smoothly achieved.

Also, in the embodiment, when the processing on the rack set in drawer 30 is started and transferring the sample tube in the rack is started, drawer 30 is locked. Accordingly, it can be prevented that the rack in which transferring the sample tube is started is wrongly pulled out to block the transfer of the sample tube by tube transfer unit 50.

Also, in the embodiment, it is detected whether or not a sample tube is in a holding position when a gripping operation is performed by grippers 541, 542 in the holding position. When the sample tube is not held, the transfer operation for the sample tube to this holding position is suspended. Accordingly, the unnecessary transfer operation by tube transfer unit 50 can be avoided and the transfer of the sample tube can be effectively continued.

Also, in the embodiment, corresponding drawer 30 can be forwardly pulled out and the rack can be set in this drawer 30 when lamp 22 is lit in green and when lamp 22 is lit off. When lamp 22 flashes in green, drawer 30 cannot be forwardly pulled out and the rack cannot be set in this drawer 30. Accordingly, an operator can intuitively see whether or not corresponding drawer 30 can be set in the rack by checking the state of lamp 22. Thus, the sample tube may be smoothly replaced.

As described above, the embodiment is described. However, the invention is not limited to the embodiment, and various modifications are possible in addition to the embodiment of the invention.

For example, in the above embodiment, a device to which the invention is applied is assumed to be sample analyzer 1 to analyze blood. However, it is not limited to this. The invention may be applied to a sample processing apparatus to perform processing on a sample, such as an immunity analyzer, gene amplification measurement device, biochemical analyzer, urine qualitative analyzer, in-urine physical component analyzer, or blood smear creation device.

Also, a transfer path of a sample tube is not limited to those described in the above-described embodiment and may be modified as appropriately.

Figure 13A:
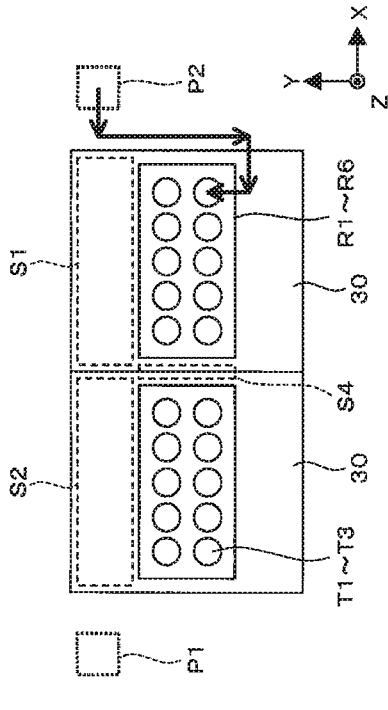
FIGS. 13A to 13D are diagrams, each illustrating a path in which sample tubes held in the left rack according to a modified embodiment are transferred by a tube transfer unit.
Figure 13B:
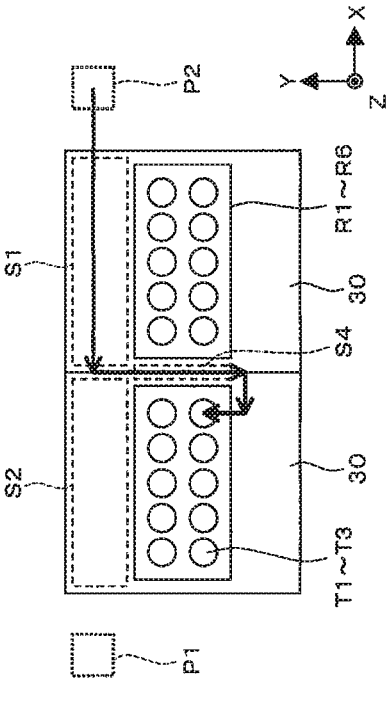
Figure 13C:
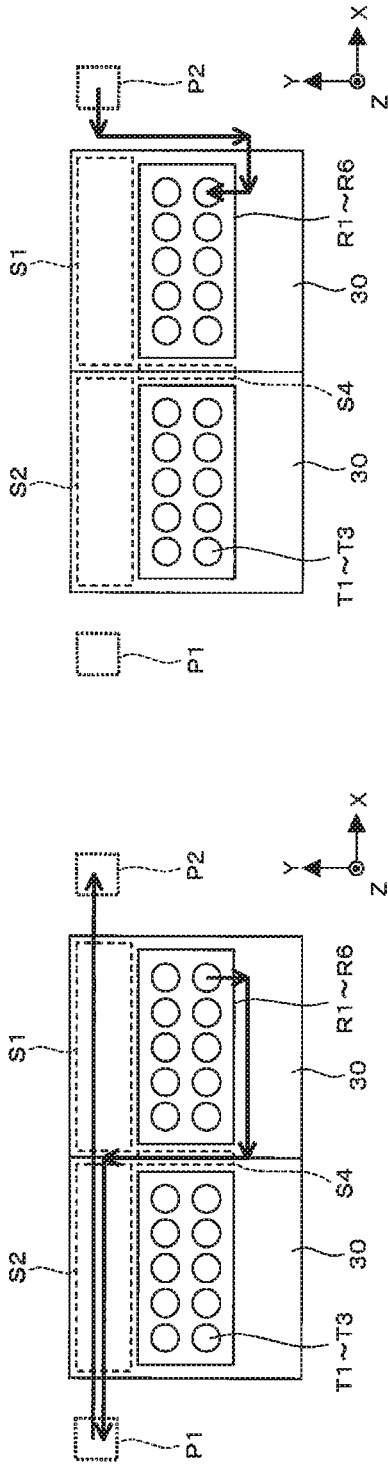
Figure 13D:
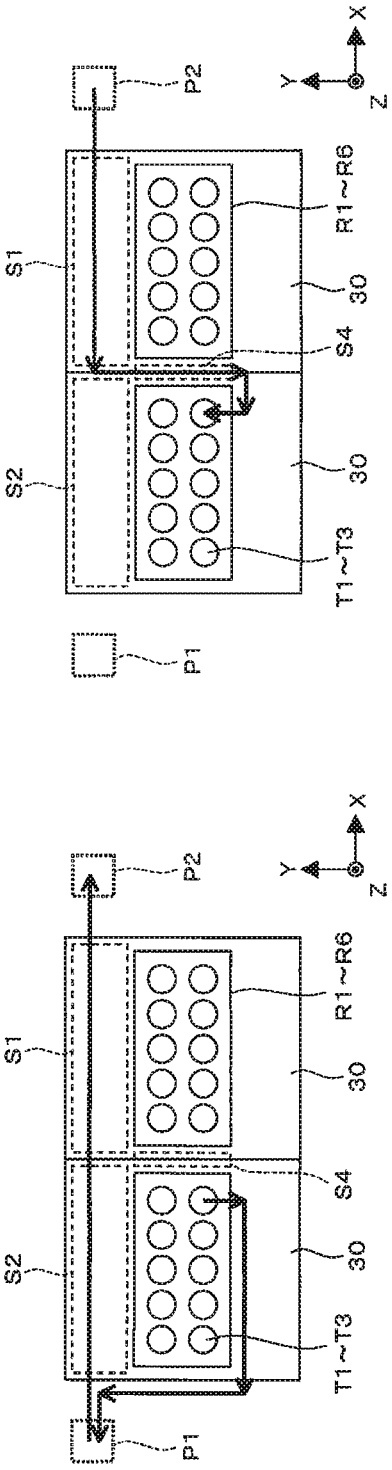

For example, in the embodiment, the sample tube taken out from the front row of the rack is transferred to the left in space S3 after being slightly transferred backwardly. However, the embodiment is not limited to this. As illustrated in FIGS. 13A and 13C, the taken-out sample tube may be conveyed to the left in a space on the front of the rack after being slightly forwardly transferred. It is to be noted in this case that the sample tube to be returned from position P2 to the original holding position of the rack is transferred as illustrated in FIGS. 13B and 13D.

In this manner, after the sample tube is transferred, space S3 is no longer used for transfer. Accordingly, it is no longer necessary to provide the gap between the front and rear rows of the rack as described in the embodiment. Thus, as illustrated in FIGS. 13A to 13D, the width of the rack in the back and forth direction can be reduced, so that miniaturization of the rack can be achieved. However, when the rack is configured with a small gap between the front and rear rows, the rack easily tends to tilt in the back and forth directions. Accordingly, in order for the rack to stably stand up for itself, it is preferable to provide space S3 as described in the embodiment. Also, in the cases of FIGS. 13A to 13D, since the sample tube travels in front of the rack, the transfer distance is longer than that in the embodiment. For this reason, to shorten the transfer time, it is preferable to provide space S3 and use space S3 as a conveyance path as described in the embodiment.

In addition, in the embodiment, the sample tube taken out from the front row of the right rack is transferred to the left in space S3 and is backwardly transferred in space S4. Also, the sample tube to be returned from position P2 to the front row of the left rack is forwardly transferred in space S4 and is transferred to the left in space S3. However, the embodiment is not limited to this. As illustrated in FIG. 14A, the sample tube taken out from the front row of the right rack may be transferred to the right in space S3 and be backwardly transferred in the space on the right side of the right rack. Also, as illustrated in FIG. 14D, the sample tube to be returned to the front row of the left rack from position P2 may be forwardly transferred in the space on the left side of the left rack and be transferred to the right in space S3. It is to be noted that in this case that, as similar to the embodiment, the sample tube to be returned to the front row of the right rack from position P2 and the sample tube taken out from the front row of the left rack are respectively transferred as illustrated in FIGS. 14B and 14C.

In this manner, after the sample tube is transferred, space S4 is no longer used for transfer. Accordingly, it is no longer necessary to provide the gap between the right and left racks as described in the embodiment. Thus, as illustrated in FIGS. 14A to 14D, the gap between the right and left racks can be reduced, so that miniaturization of sample analyzer 1 can be achieved. However, in this transfer path, since the sample tube travels around the right side of the right rack as illustrated in FIG. 14A and the sample tube travels around the left side of the left rack as illustrated in FIG. 14D, the transfer distance is longer than that in the embodiment. For this reason, to shorten the transfer time, it is preferable to provide space S4 and use space S4 as a conveyance path as described in the embodiment.

In addition, in the embodiment, the sample tube to be returned to the front row of the right rack from position P2 is forwardly transferred in the space on the right side of the right rack and is transferred to the left in space S3. Also, the sample tube taken out from the front row of the left rack is transferred to the left in space S3 and is backwardly transferred in the space on the left side of the left rack. However, the embodiment is not limited to this. As illustrated in FIG. 15B, the sample tube to be returned from position P2 to the front row of the right rack may be forwardly transferred in space S4 and be transferred to the right in space S3. Also, as illustrated in FIG. 15C, the sample tube taken out from the front row of the left rack may be transferred to the right in space S3 and be backwardly transferred in space S4. It is to be noted in this case that, as similar to the embodiment, the sample tube taken out from the front row of the right rack and the sample tube to be returned to the front row of the left rack from position P2 are respectively transferred as illustrated in FIGS. 15A and 15D.

As described above, after the sample tube is transferred, the space on the right side of the right rack and the space on the left side of the left rack are no longer used for transfer. Accordingly, mechanism inside sample analyzer 1 can be provided therein, so that miniaturization of sample analyzer 1 can be achieved. However, in this transfer path, since the sample tube travels around the left side of the right rack as illustrated in FIG. 15B and the sample tube travels around the right side of the left rack as illustrated in FIG. 15C, the transfer distance is longer than that in the embodiment. For this reason, to shorten the transfer time, it is preferable that the space on the right side of the right rack and the space on the left side of the left rack be used for the conveyance path.

Also, in the embodiment, the sample tubes taken out from the rear row of the right and left racks are transferred as illustrated in FIGS. 11C and 12C, and the sample tubes to be returned to the rear row of the right and left racks from position P2 are transferred as illustrated in FIG. 11D and FIG. 12D. However, the embodiment is not limited to this. The sample tubes taken out from the rear row of the right and left racks may be transferred passing space S3 after being slightly forwardly transferred. Also, the sample tubes to be returned from position P2 to the rear row of the right and left racks may be returned to the original holding position after being transferred passing space S3. However, even in the case of these paths, the transfer distance of the sample tube is longer than that in the embodiment. Thus, to shorten the transfer time, it is preferable that the transmission path in the embodiment be used.

Also, in the embodiment, two drawers 30 capable of being drawn out from the front side of main body 2 are arranged side by side. The embodiment is not limited to this. Three or more drawers 30 may be arranged side by side. In this case, positions P1 and P2 are respectively provided on the rear left and rear right sides of drawers 30 arranged side by side, and sample tubes are transferred in a path passing behind other rack.

Also, in the embodiment, the stirring processing on the sample tube is performed in position P1, but the embodiment is not limited to this. Other processing may be performed in position P1. For example, when the sample tube is stirred in the conveyance path by back-forth conveyance unit 70, barcode label Tc of the sample tube may be read in position P1.

Also, in the embodiment, the rack is configured to be detachably attached to drawer 30. However, the rack does not necessarily have to be configured to be detachably attached to drawer 30. In the embodiment, the kind of the sample tube is identified by the shape of the rack. However, for example, when kinds of sample tubes are manually inputted, the attachable/detachable rack does not have to be used and the rack may be integrated with drawer 30. However, even in a case where kinds of sample tubes are manually inputted, it is better to use the attachable/detachable rack because the sample tubes can be replaced all together at once and thus workability and convenience can be improved.

Also, in the embodiment, the rack has the configuration in which five holders Ra are arranged in two rows. However, the embodiment is not limited to this. Holders Ra may be provided in three or more rows in the rack or holders Ra may be provided in one row in the rack.

Also, in the embodiment, the rack is set in drawer 30 so that five holders Ra arranged in left and right directions in the two rows in the back and forth directions. However, the embodiment is not limited to this. The rack may be set in drawer 30 so that five holders Ra arranged in the back and forth directions are arranged in two rows in the right and left directions (pulled out direction of drawer 30). In other words, the moving direction of drawer 30 and the rows of holders Ra may be in parallel. In this case, rack set unit 300 of drawer 30 is configured to be rotated by 90 degrees in the X-Y plane and grippers 541, 542 are configured to be rotated by 90 degrees in the X-Y plane.

Also, in the embodiment, the width of center portion Rb of the rack in the back and forth directions is set so to be slightly larger than the diameter of body portion Ta of the sample tube. However, the embodiment is not limited to this. It is only needed that the sample tube to be transferred by tube transfer unit 50 can be transferred in the right and left directions in space S3 formed by center portion Rb. However, when the width of center portion Rb in the back and forth directions is set larger, the size of the rack is also increased. Thus, it is preferable that center portion Rb be configured as small as possible as described in the embodiment.

Also, in the embodiment, spaces S1, S2, and S4 are formed as small as an extent that tube transfer unit 50 is capable of transferring the sample tube. However, the embodiment is not limited to this. Spaces S1, S2, and S4 may be formed to be larger than that in the embodiment. However, when the sizes of spaces S1, S2, and S4 are increased, the size of sample analyzer 1 is also increased. Thus, it is preferable that spaces S1, S2, and S4 be formed as small as possible as described in the embodiment.

Also, in the embodiment, when the transfer operation for the sample tube is started with respect to the rack set in drawer 30, this drawer 30 is locked. However, the embodiment is not limited to this. Drawer 30 may be locked at a predetermined timing after the transfer operation of the sample tube is started. For example, after the transfer operation of the sample tube with respect to the rack is started and before grippers 541, 542 reach an area above the rack, drawer 30 may be locked. It is preferable that drawer 30 be locked at least during a period of time in which grippers 541, 542 or the sample tube gripped by grippers 541, 542 and the sample tube held in the rack interfere with each other when drawer 30 is pulled out.

Also, in the above-described embodiment, the state of drawer 30 is displayed by display of lamp 22. However, it may be always displayed by display input unit 3.

Also, in the embodiment, spaces S1, S2 through which the sample tube passes are provided above two drawers 30. However, the way to provide spaces S1, S2 is not limited to this. For example, spaces S1, S2 may be provided to the rear of the back sides of drawers 30 in the state where two drawers 30 are closed.

In this way the embodiments described above provide a sample analyzer and a rack that enable sample tube replacement in a sample tube set unit even during measurement.

The invention claimed is:

1. A sample processing apparatus that processes samples in sample tubes held in a first rack and a second rack each having fixed positions to hold the sample tubes, the sample processing apparatus comprising:
   a case;
   a first drawer, which is slidable into and out of the case, the first drawer configured to support the first rack;
   a second drawer, which is slidable into and out of the case, the second drawer configured to support the second rack;
   a lock mechanism provided in the case and configured to lock the first drawer and the second drawer;
   a tube set unit that is provided in the case and in which one sample tube is placeable;
   a tube transfer unit, which is provided in the case and is configured to transfer one sample tube of the sample tubes from one of the first rack supported by the first drawer and the second rack supported by the second drawer into the tube set unit;
   an aspiration unit, which is provided in the case and configured to aspirate a sample in the sample tube transferred into the tube set unit; and
   a processor configured to execute a computer program to perform operations comprising:
      causing the lock mechanism to lock the first drawer so as not to slide out of the case and causing the lock mechanism not to lock the second drawer so as to be capable of sliding out of the case, in a condition in which: the sample tube is being transferred from the first rack by the tube transfer unit; or the sample tube transferred from the first rack is in the tube set unit.

2. The sample processing apparatus according to claim 1, wherein
   the processor is configured to perform operations further comprising:
   causing the lock mechanism to lock the first drawer so as not to slide out of the case until the aspiration unit aspirates the sample in each of the sample tubes transferred from the first rack and the tube transfer unit transfers each of the sample tubes to the first rack.

3. The sample processing apparatus according to claim 1, wherein the lock mechanism comprises a first lock mechanism unit and a second lock mechanism unit configured to lock the first drawer and the second drawer, respectively, such that the first drawer and the second drawer are prevented from sliding out of the case.

4. The sample processing apparatus according to claim 1, wherein the tube transfer unit comprises:
   a pair of grippers; and
   a detector, wherein
      the pair of grippers is configured to grip one sample tube of sample tubes in the first rack supported by the first drawer and the second rack supported by the second drawer in a gripping position; and
      the detector is configured to detect a presence of the one sample tube.

5. The sample processing apparatus according to claim 1, further comprising a display, wherein
   the processor is configured to perform operations further comprising causing the display to display an availability of the first drawer and the second drawer for supporting the first rack and the second rack.

6. The sample processing apparatus according to claim 1, further comprising a first light and a second light unit provided respectively for the first drawer and the second drawer, wherein
   the processor is configured to perform operations further comprising:
      activating the first light in a first mode, in a condition in which the first drawer is slidable out of the case;
      activating the first light in a second mode different from the first mode, in a condition in which the first drawer is not slidable out of the case;
      activating the second light in the first mode, in a condition in which the second drawer is slidable out of the case; and
      activating the second light in the second mode, in a condition in which the second drawer is not slidable out of the case.

7. The sample processing apparatus according to claim 1, wherein
   the first drawer in the case supports the first rack such that a first space is provided behind the first rack in a sliding direction of the first drawer into the case,
   the tube set unit is provided closer to the first drawer than to the second drawer in the case; and
   the processor is configured to perform operations further comprising causing the tube transfer unit to transfer the sample tube from the second rack into the tube set unit through the first space.

8. The sample processing apparatus according to claim 7, wherein
   the first drawer comprises a rack set unit that supports the first rack; and
   an area of the first drawer corresponding to the first space is provided between the rack set unit of the first drawer and an end side of the first drawer in the sliding direction of the first drawer.

9. The sample processing apparatus according to claim 1, wherein
   the processor is configured to perform operations further comprising causing the tube transfer unit to transfer the sample tube at a height level at which a lower end of the sample tube is located adjacent to an upper surface of the first rack supported by the first drawer.

10. The sample processing apparatus according to claim 7, further comprising:
   a stir unit provided closer to the second drawer than to the first drawer in the case and configured to perform a stirring operation to the sample tube transferred from the one of the first rack and the second rack, wherein
   the second drawer comprises a rack set unit that supports the second rack;
   an area of the second drawer corresponding to a second space is provided between the rack set unit of the second drawer and an end side of the second drawer in a sliding direction of the second drawer; and the processor is configured to perform operations further comprising causing the tube transfer unit to transfer the sample tube from the first rack, though the first space and the second space, to the stir unit.

11. The sample processing apparatus according to claim 7, wherein
at least one of the first rack and the second rack comprises:
tube holders capable of holding the sample tubes, respectively; and
an area corresponding to a second space;
the tube holders are integrally provided with the area corresponding to the second space and arranged in a row in the area corresponding to the second space, and
the processor is configured to perform operations further comprising causing the tube transfer unit to transfer the sample tube through the second space.

12. The sample processing apparatus according to claim 7, wherein
the first rack and the second rack are provided adjacent to each other across a second space, and
the processor is configured to perform operations further comprising causing the tube transfer unit to transfer the sample tube through the second space.

13. The sample processing apparatus according to claim 1, further comprising:
a sample preparation unit; and
a detector, wherein
the sample preparation unit prepares a measurement sample by mixing the sample aspirated by the aspiration unit and a reagent; and
the detector generates a detection signal from the measurement sample.

14. The sample processing apparatus according to claim 1, wherein the samples in the sample tubes processed by the sample processing apparatus comprise blood.

15. The sample processing apparatus according to claim 1, further comprising a conveyance unit provided in the case, wherein the conveyance unit moves the tube set unit between a set position in which the sample tube transferred from the one of the first rack and the second rack is set in the tube set unit and an aspiration position in which the sample in the sample tube is aspirated by the aspiration unit.

16. The sample processing apparatus according to claim 1, further comprising a first lamp and a second lamp respectively provided for the first drawer and the second drawer, wherein
the processor is configured to perform operations further comprising:
activating the first lamp based on whether the processor performs an operation causing the lock mechanism not to lock the first drawer; and
activating the second lamp based on whether the processor performs an operation causing the lock mechanism not to lock the second drawer.

17. A sample processing apparatus that processes samples in sample tubes held in a first rack and a second rack each having fixed positions to hold the sample tubes, comprising:
a case;
a first drawer, which is slidable into and out of the case, the first drawer configured to support the first rack;
a second drawer, which is slidable into and out of the case, the second drawer configured to support the second rack;
a lock mechanism provided in the case and configured to lock the first drawer and the second drawer;
a tube set unit that is provided in the case and in which one sample tube is placeable;
a tube transfer unit, which is provided in the case and is configured to transfer one sample tube of sample tubes from one of the first rack supported by the first drawer and the second rack supported by the second drawer into the tube set unit;
an aspiration unit, which is provided in the case and configured to aspirate a sample in the sample tube transferred into the tube set unit; and
a processor configured to execute a computer program to perform operations comprising:
in a condition in which the first drawer is out of the case for a replacement of the first rack, causing the tube transfer unit to transfer the sample tube from the second rack into the tube set unit; and causing the lock mechanism to lock the second drawer so as not to be slidable out of the case.

18. The sample processing apparatus according to claim 17, wherein
in a condition in which the first drawer is in the case and supports another rack after the replacement of the first rack, the processor is configured to perform operations further comprising:
causing the tube transfer unit to transfer all of the sample tubes from the second rack into the tube set unit, and then
causing the tube transfer unit to transfer pick one sample tube of sample tubes from the another rack supported by the first drawer into the tube set unit.

19. The sample processing apparatus according to claim 17, wherein
processor is configured to perform operations further comprising: causing the tube transfer unit to transfer the sample tube from the tube set unit to the second rack supported by the second drawer after the aspiration unit aspirates the sample in the sample tube transferred by the tube transfer unit from the second rack into the tube set unit.

* * * * *